US011583282B2

(12) United States Patent
Gorochow et al.

(10) Patent No.: US 11,583,282 B2
(45) Date of Patent: Feb. 21, 2023

(54) LAYERED BRAIDED ANEURYSM TREATMENT DEVICE

(71) Applicant: DePuy Synthes Products, Inc., Raynham, MA (US)

(72) Inventors: Lacey Gorochow, Raynham, MA (US); Ariel Soto Del Valle, Raynham, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 120 days.

(21) Appl. No.: 16/847,284

(22) Filed: Apr. 13, 2020

(65) Prior Publication Data

US 2020/0367898 A1  Nov. 26, 2020

Related U.S. Application Data

(62) Division of application No. 16/418,199, filed on May 21, 2019, now Pat. No. 10,653,425.

(51) Int. Cl.
*A61B 17/12* (2006.01)

(52) U.S. Cl.
CPC .. *A61B 17/12113* (2013.01); *A61B 17/12031* (2013.01); *A61B 17/12168* (2013.01); *A61B 2017/12054* (2013.01)

(58) Field of Classification Search
CPC ........ A61B 17/12022; A61B 17/12031; A61B 17/12109; A61B 17/12113; A61B 17/1214; A61B 17/12145; A61B 17/12168; A61B 17/12172
See application file for complete search history.

(56) References Cited

U.S. PATENT DOCUMENTS

| | | | |
|---|---|---|---|
| 2,849,002 | A | 8/1958 | Oddo |
| 3,480,017 | A | 11/1969 | Shute |
| 4,085,757 | A | 4/1978 | Pevsner |
| 4,282,875 | A | 4/1981 | Serbinenko et al. |
| 4,364,392 | A | 12/1982 | Strother et al. |
| 4,395,806 | A | 8/1983 | Wonder et al. |
| 4,517,979 | A | 5/1985 | Pecenka |

(Continued)

FOREIGN PATENT DOCUMENTS

| | | |
|---|---|---|
| CA | 2395796 A1 | 7/2001 |
| CA | 2 431 594 A1 | 9/2002 |

(Continued)

OTHER PUBLICATIONS

Extended European Search Report issued in corresponding European Patent Application No. 19 21 5277 dated May 12, 2020.

(Continued)

*Primary Examiner* — Todd J Scherbel
(74) *Attorney, Agent, or Firm* — Troutman Pepper Hamilton Sanders LLP

(57) ABSTRACT

A braided implant is provided that can secure within an aneurysm sac, occlude a majority of the aneurysm's neck, and at least partially fill the aneurysm sac. The implant can include a tubular braid that can be set into a predetermined shape, compressed for delivery through a microcatheter, and implanted in at least one implanted position. In some examples, the tubular braid can be implanted in two distinct implanted shapes, allowing for treatment of a wide range of aneurysm sizes. In some examples, the implanted braid can include a compaction resistant column spanning the height of the aneurysm.

18 Claims, 15 Drawing Sheets

(56) References Cited

U.S. PATENT DOCUMENTS

| | | |
|---|---|---|
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,916,235 A | 6/1999 | Guglielmi |
| 5,891,128 A | 7/1999 | Yen et al. |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi et al. |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lilip et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,377,932 B2 | 5/2008 | Mitelberg et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,974,512 B2 | 3/2015 | Aboytes et al. |
| 8,992,568 B2 | 3/2015 | Duggal et al. |
| 8,998,947 B2 | 4/2015 | Aboytes et al. |
| 9,055,948 B2 | 6/2015 | Jaeger et al. |
| 9,107,670 B2 | 8/2015 | Hannes et al. |
| 9,161,758 B2 | 10/2015 | Figulla et al. |
| 9,232,992 B2 | 1/2016 | Heidner |
| 9,259,337 B2 | 2/2016 | Cox et al. |
| 9,314,326 B2 | 4/2016 | Heidner et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |

(56) References Cited

U.S. PATENT DOCUMENTS

| | | |
|---|---|---|
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,681,861 B2 | 6/2017 | Heisei et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,826,980 B2 | 11/2017 | Figulla et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,004,510 B2 | 6/2018 | Gerberding |
| 10,130,372 B2 | 11/2018 | Griffin |
| 10,307,148 B2 | 6/2019 | Heisei et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,653,425 B1 | 5/2020 | Gorochow et al. |
| 10,716,573 B2 | 7/2020 | Connor |
| 10,743,884 B2 | 8/2020 | Lorenzo |
| 10,751,066 B2 | 8/2020 | Lorenzo |
| 11,464,518 B2 | 10/2022 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy et al. |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace et al. |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0119886 A1 | 5/2008 | Greenhalgh et al. |
| 2008/0281350 A1 | 11/2008 | Sepetka |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1 | 10/2013 | Cox et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0257361 A1 | 9/2014 | Prom |

(56) References Cited

U.S. PATENT DOCUMENTS

| | | |
|---|---|---|
| 2014/0277013 A1 | 9/2014 | Sepetka et al. |
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2016/0249935 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0114350 A1 | 4/2017 | dos Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0258473 A1 | 9/2017 | Plaza et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1 | 5/2018 | Connor |
| 2018/0206850 A1 | 7/2018 | Wang et al. |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0142567 A1 | 5/2019 | Janardhan et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0357914 A1 | 11/2019 | Gorochow et al. |
| 2019/0365385 A1 | 12/2019 | Gorochow |
| 2020/0000477 A1 | 1/2020 | Nita et al. |
| 2020/0069313 A1 | 3/2020 | Xu et al. |
| 2020/0268365 A1 | 8/2020 | Hebert et al. |
| 2020/0375606 A1 | 12/2020 | Lorenzo |
| 2021/0007755 A1 | 1/2021 | Lorenzo et al. |
| 2021/0177429 A1 | 6/2021 | Lorenzo |

FOREIGN PATENT DOCUMENTS

| | | |
|---|---|---|
| CA | 2598048 A1 | 5/2008 |
| CN | 204 683 687 U | 7/2015 |
| CN | 107374688 A | 11/2017 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |

(56) References Cited

FOREIGN PATENT DOCUMENTS

| | | |
|---|---|---|
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| EP | 3 636 173 A2 | 10/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2014-522268 A | 9/2014 |
| JP | 2016-502925 A | 2/2015 |
| JP | 2016-502925 A | 2/2016 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | 2005/117718 A1 | 12/2005 |
| WO | WO 2005117718 A1 | 12/2005 |
| WO | WO 2006034149 A2 | 3/2006 |
| WO | WO 2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A2 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | 2015/160721 A1 | 10/2015 |
| WO | WO 2015160721 A1 | 10/2015 |
| WO | 2015/171268 A2 | 11/2015 |
| WO | WO 2015166013 A1 | 11/2015 |
| WO | WO 2015171268 A2 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2017/161283 A1 | 9/2017 |
| WO | WO 2018051187 A1 | 3/2018 |
| WO | WO 2019/038293 A1 | 2/2019 |
| WO | WO 2012/034135 A1 | 3/2021 |

OTHER PUBLICATIONS

Extended European Search Report issued in corresponding European Patent Application No. 20 21 2968 dated May 11, 2021.
File History for corresponding U.S. Appl. No. 16/418,199 in parent application U.S. Appl. No. 16/418,199.
Altes et al., Creation of Saccular Aneurysms in the Rabbit: A Model Suitable for Testing Endovascular Devices. AJR 2000; 174: 349-354.
Schaffer, Advanced Materials & Processes, Oct. 2002, pp. 51-54.

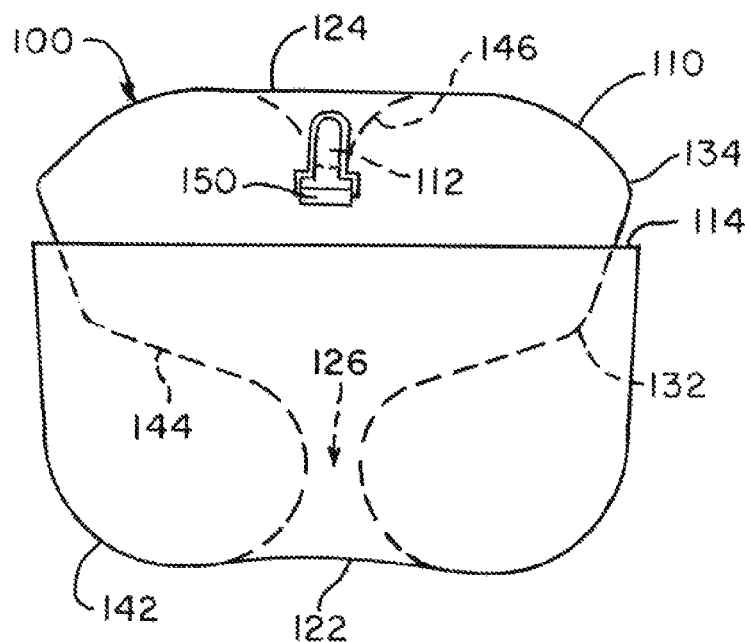
FIG. 1A
FIG. 1B
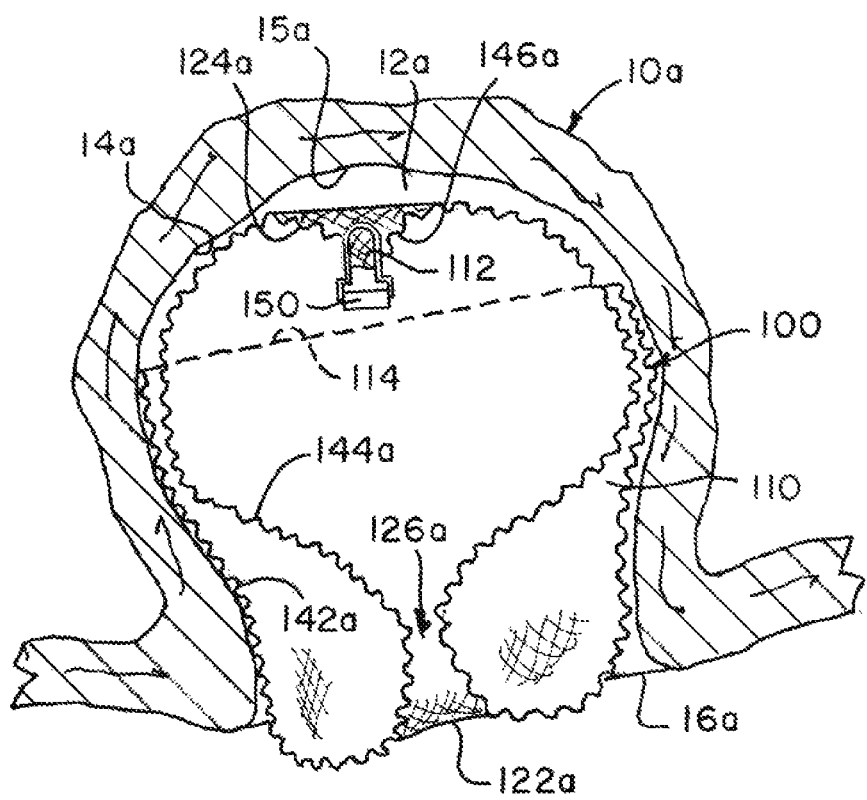

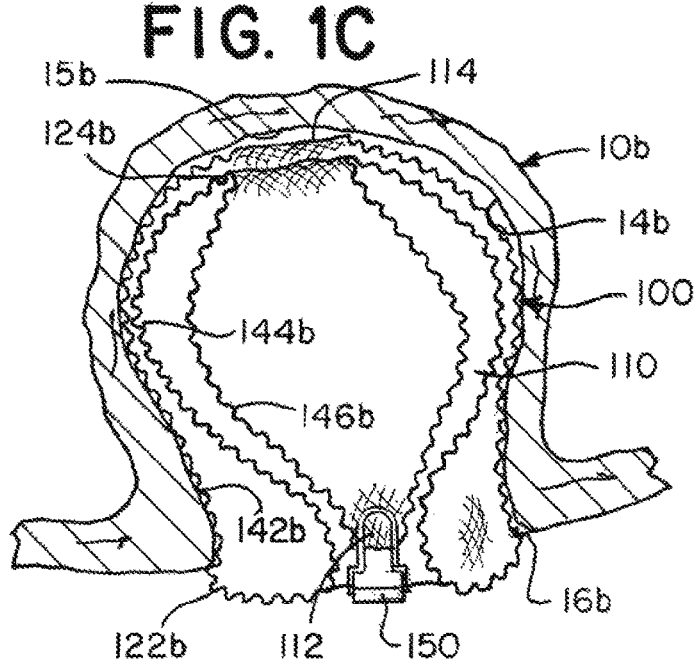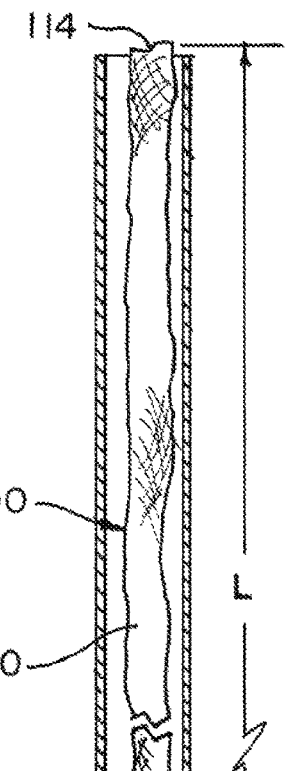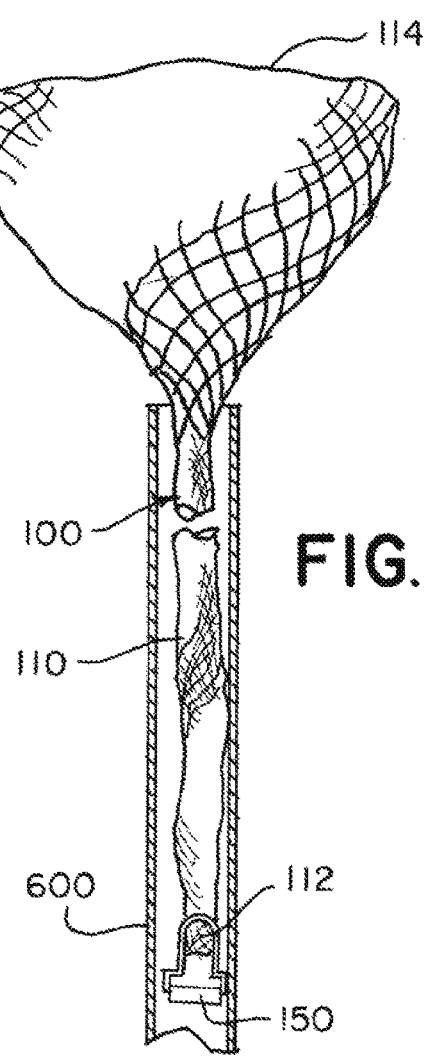

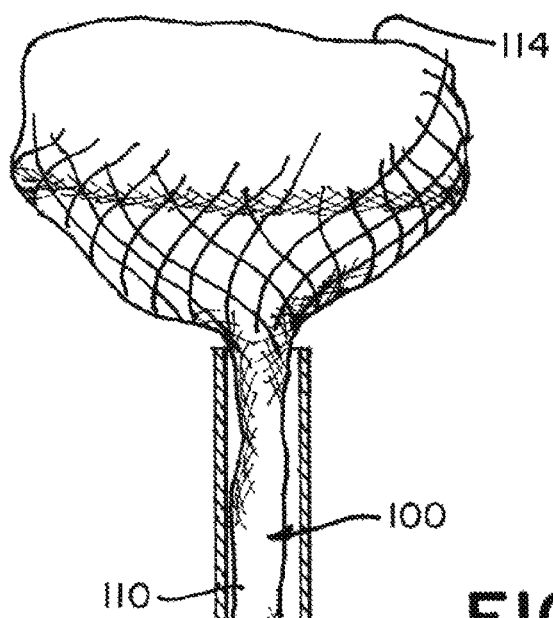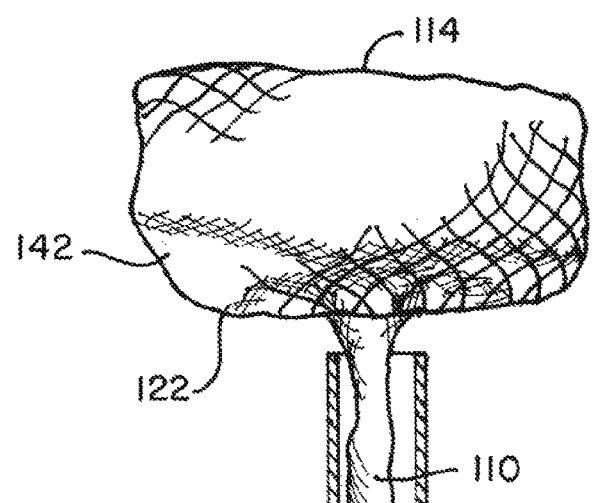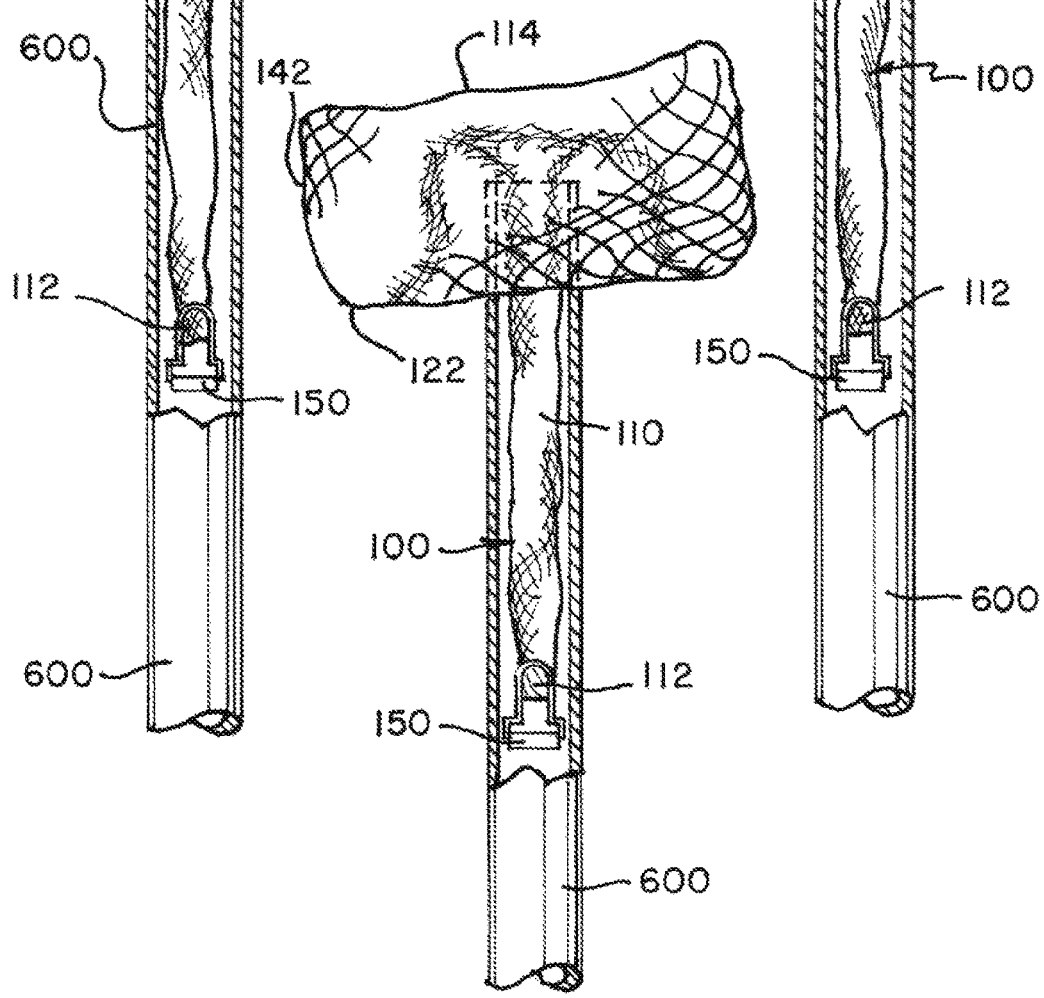

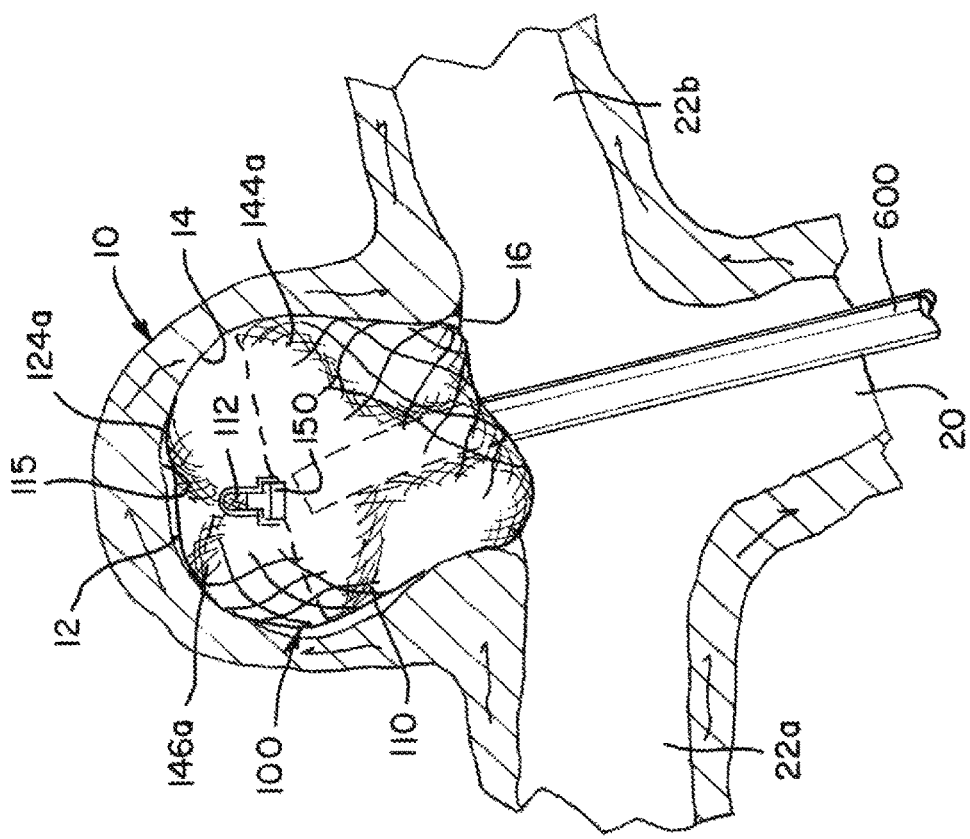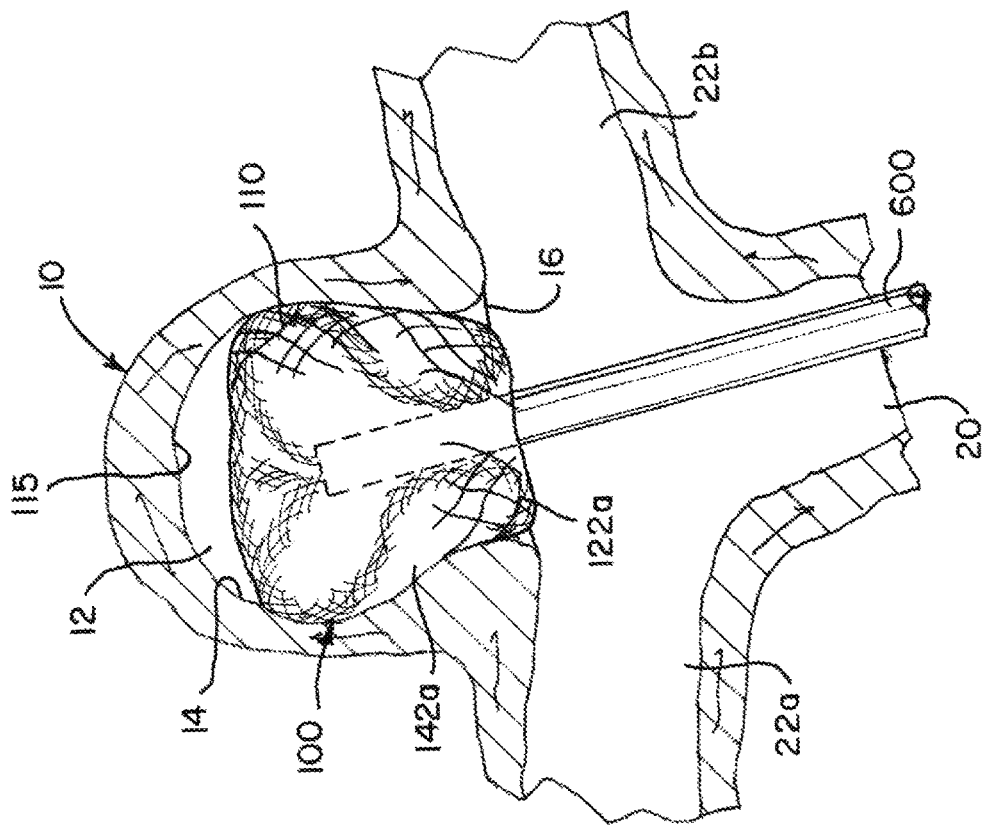

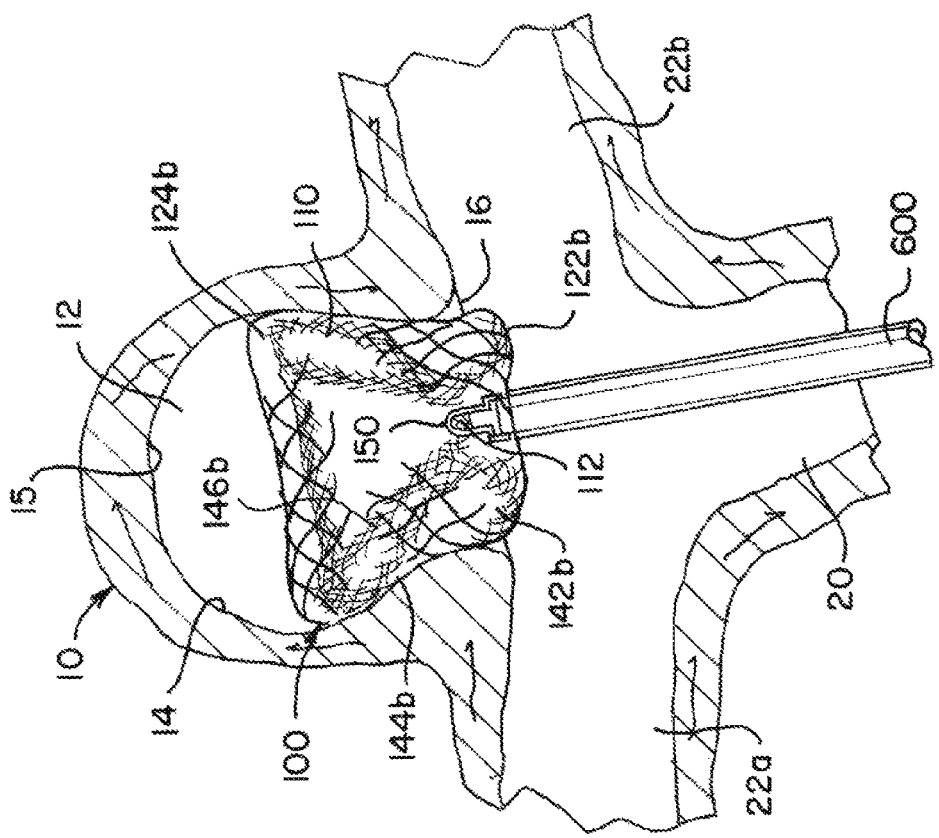
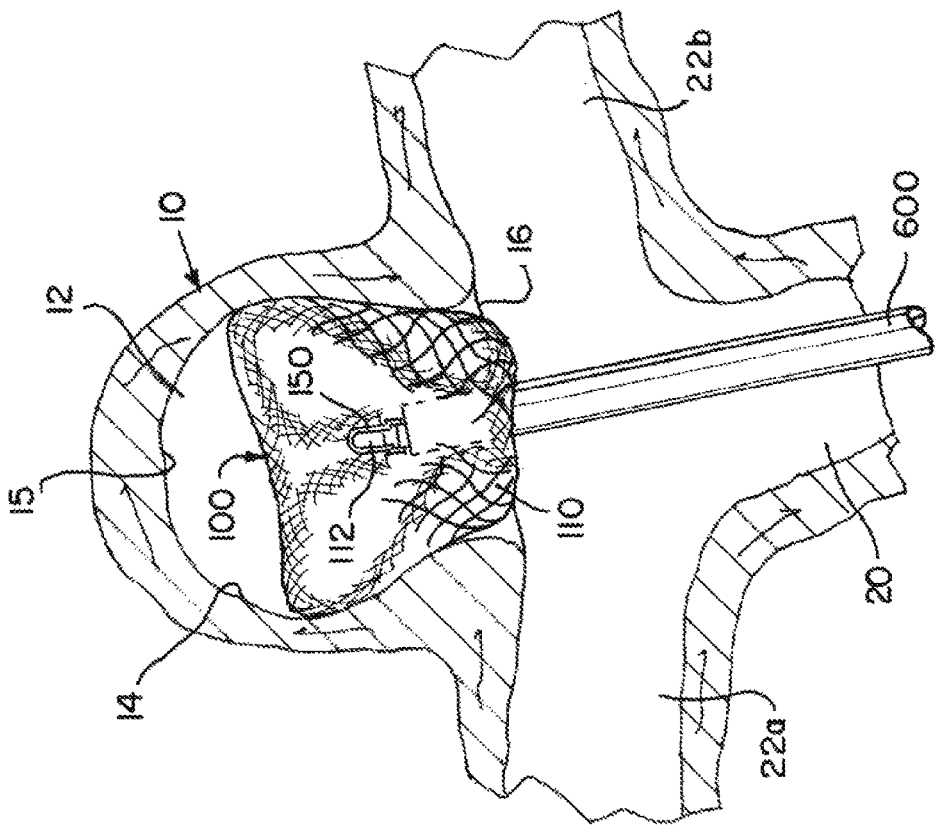

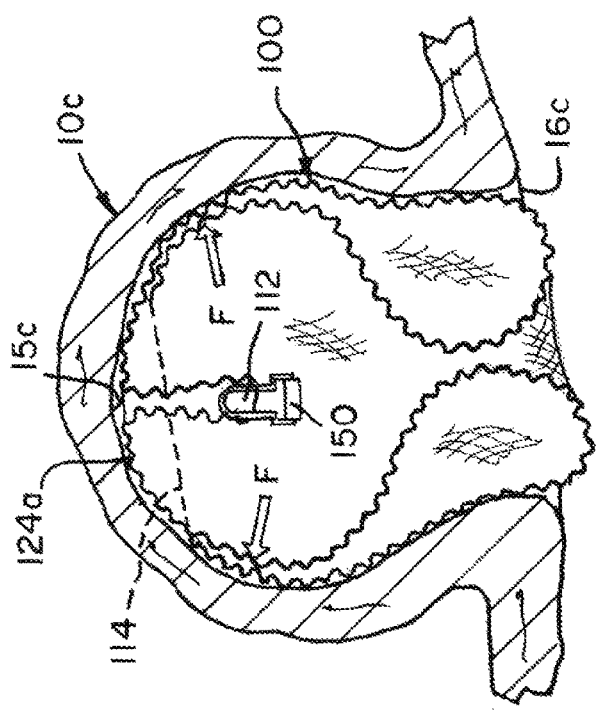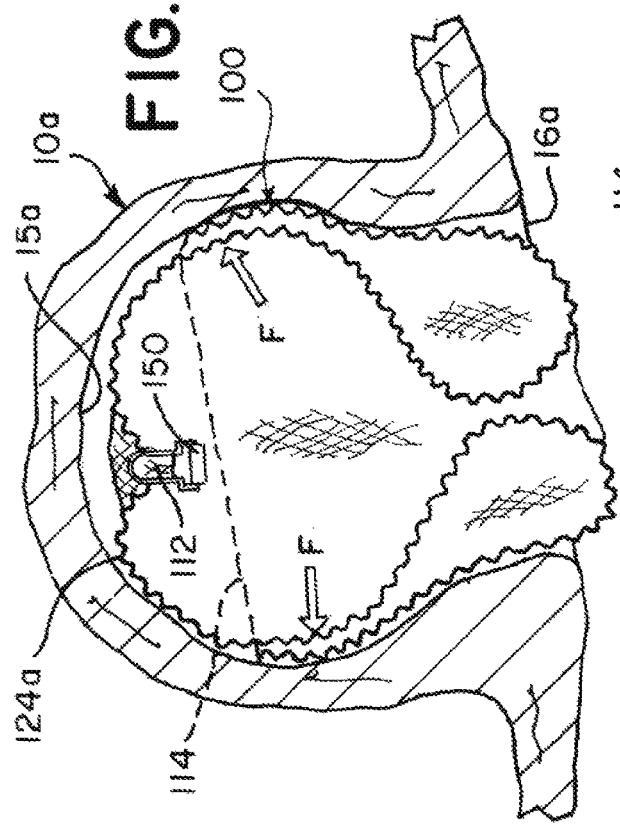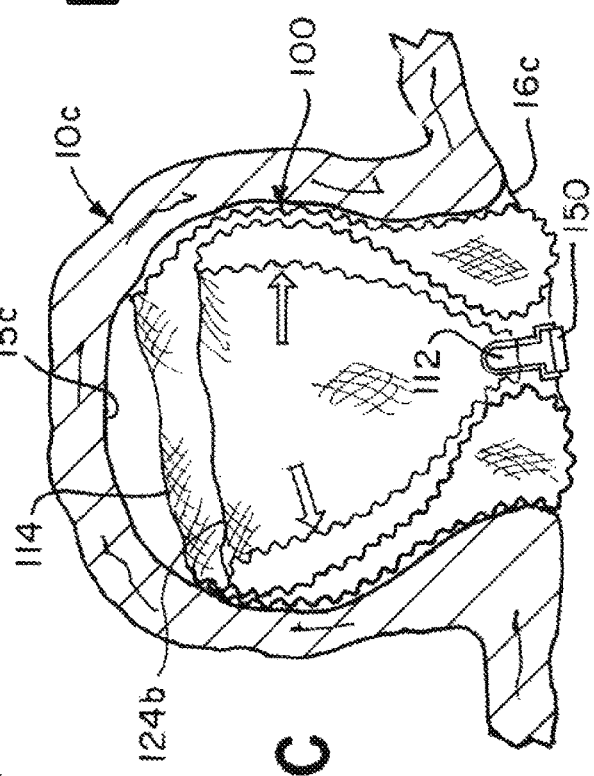

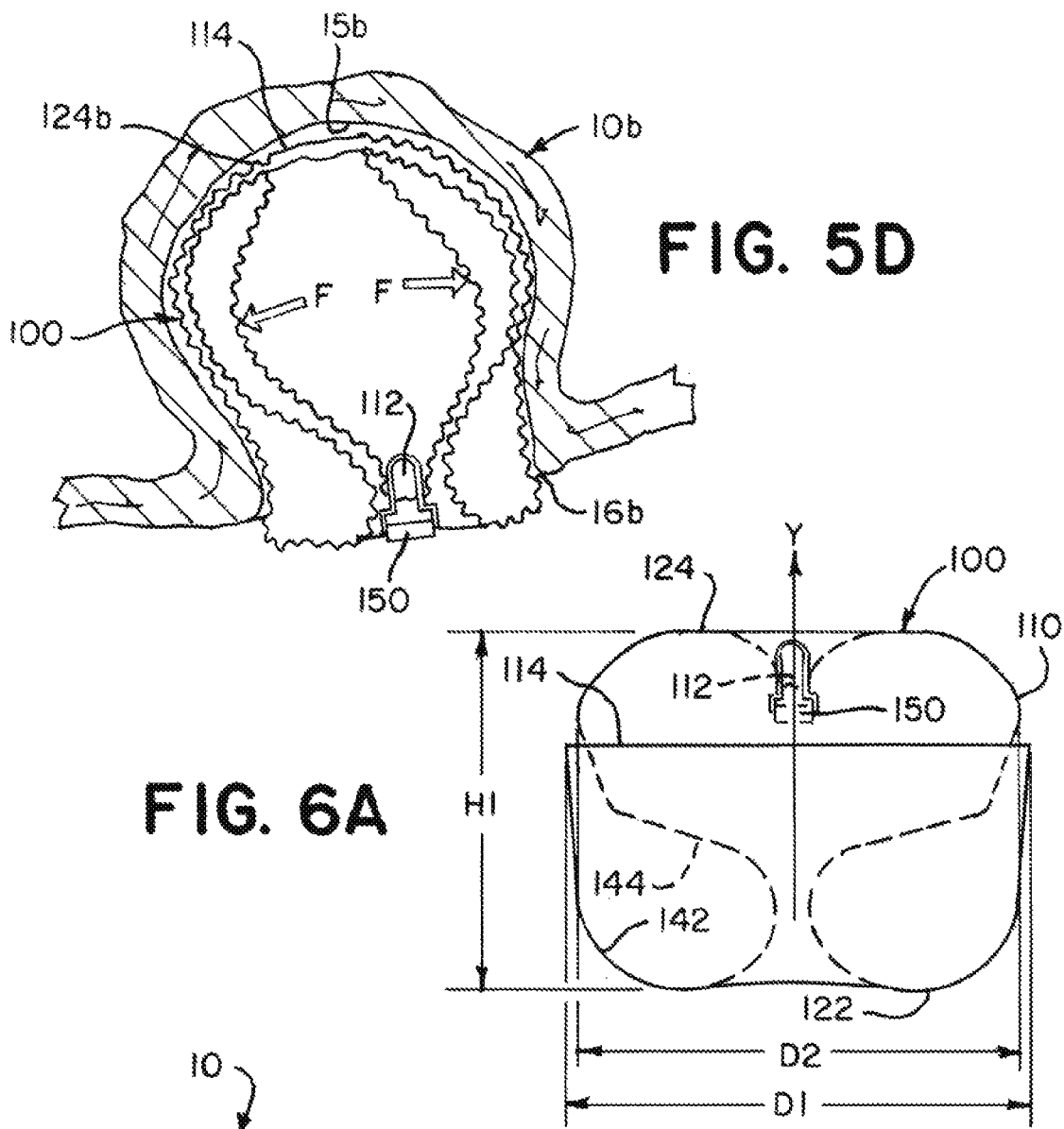
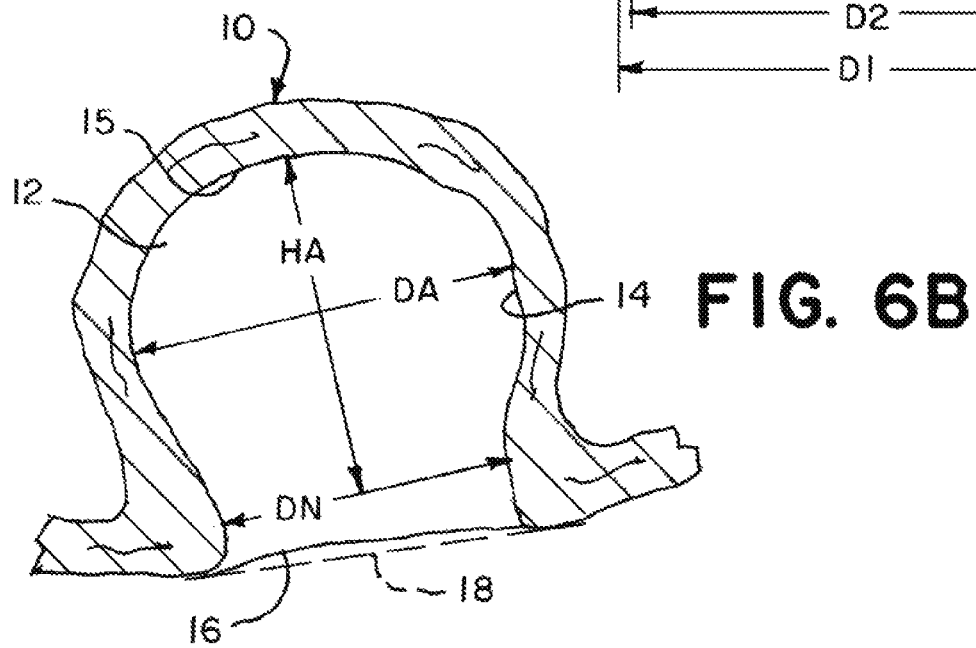

LAYERED BRAIDED ANEURYSM TREATMENT DEVICE

CROSS-REFERENCE TO RELATED APPLICATIONS

The present application is a divisional application of U.S. patent application Ser. No. 16/418,199 filed May 21, 2019, the contents of which are incorporated by reference as if set forth in its entirety herein.

FIELD OF INVENTION

The present invention generally relates to medical instruments, and more particularly, to embolic implants for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include intravascularly delivered treatment devices that fill the sac of the aneurysm with embolic material or block the entrance or neck of the aneurysm. Both approaches attempt to prevent blood flow into the aneurysm. When filling an aneurysm sac, the embolic material clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm.

Current intravascularly delivered devices typically utilize multiple embolic coils to either fill the sac or treat the entrance of the aneurysm. Naturally formed thrombotic masses formed by treating the entrance with embolic coils can result in improved healing compared to aneurysm masses packed with embolic coils because naturally formed thrombotic masses can reduce the likelihood of distention from arterial walls and facilitate reintegration into the original parent vessel shape along the neck plane. However, embolic coils delivered to the neck of the aneurysm can potentially have the adverse effect of impeding the flow of blood in the adjoining blood vessel, particularly if the entrance is overpacked. Conversely, if the entrance is insufficiently packed, blood flow can persist into the aneurysm. Treating certain aneurysm morphology (e.g. wide neck, bifurcation, etc.) can require ancillary devices such a stents or balloons to support the coil mass and obtain the desired packing density. Once implanted, the coils cannot easily be retracted or repositioned. Furthermore, embolic coils do not always effectively treat aneurysms as aneurysms treated with multiple coils often recanalize or compact because of poor coiling, lack of coverage across the aneurysm neck, blood flow, or large aneurysm size.

Alternatives to embolic coils are being explored, for example a tubular braided implant is disclosed in US Patent Publication Number 2018/0242979, incorporated herein by reference. Tubular braided implants have the potential to easily, accurately, and safely treat an aneurysm or other arterio-venous malformation in a parent vessel without blocking flow into perforator vessels communicating with the parent vessel. Compared to embolic coils, however, tubular braided implants are a newer technology, and there is therefore capacity for improved geometries, configurations, delivery systems, etc. for the tubular braided implants. For instance, delivery of tubular braided implants can require unique delivery systems to prevent the braid from inverting or abrading when pushed through a microcatheter, and some simple delivery systems that push embolic coils through microcatheters from their proximal end may not be effective to deliver tubular braids.

There is therefore a need for improved methods, devices, and systems for implants for aneurysm treatment.

SUMMARY

It is an object of the present invention to provide systems, devices, and methods to meet the above-stated needs. Generally, it is an object of the present invention to provide a braided implant that can secure within an aneurysm sac and occlude a majority of the aneurysm's neck. The implant can include a tubular braid that can be set into a predetermined shape, compressed for delivery through a microcatheter, and implanted in at least one implanted position that is based on the predetermined shape and the geometry of the aneurysm in which the braid is implanted.

In some examples presented herein, when compressed, the implant can be sufficiently short to mitigate friction forces produced when the implant is delivered unsheathed through the microcatheter allowing for a more simplistic delivery system compared to some other known braided embolic implant delivery systems.

In some examples presented herein, when the implant is implanted, a majority of the aneurysm sac can be free from embolic material to facilitate the formation of a thrombotic mass that is primarily naturally formed.

In some examples presented herein, the tubular braid can be implanted in two distinct implanted shapes, depending on the size of the aneurysm, allowing for treatment of a wider range of aneurysm sizes compared to some other known braided embolic implants.

In some examples presented herein, when implanted, the tubular braid can have a compaction resistant column extending across a majority of the height of the aneurysm and positioned centrally within the aneurysm sac.

An example implant can include a tubular braid having an open end and a pinched end. The tubular braid can have a predetermined shape that has two inversions that divide the braid into three segments. In the predetermined shape, the braid can have an outer segment that extends between the open end and a first of the two inversions, a middle segment that extends between the two inversions and is encircled by the open end, and an inner segment that extends between the second of the two inversions and the pinched end of the tubular braid and is surrounded by the middle segment.

When in the predetermined shape, the tubular braid can have a height measured between the two inversions and a substantially radially symmetrical shape having an outermost diameter. The ratio of outermost diameter to height can be between about 2:1 and about 1:3 or, more specifically, between about 2:1 and about 1:1. In the predetermined shape the middle segment can have maximum diameter that is equal to the diameter of the open end. When compressed, the tubular braid can be extended longitudinally to a single layer of braid having a length measured from the open end to the pinched end. The ratio of the outermost diameter in the predetermined shape to length in the compressed, delivery shape can be between about 0.2 and about 0.3.

The length of the tubular braid in the delivery shape can be between about 10 mm an about 40 mm, depending on the size of the aneurysm being treated.

A collection of implants, each having a uniquely shaped tubular braid can be created to provide a catalogue of implants for treating aneurysms ranging in diameter and height. Each implant in the collection can be suitable for treating aneurysms with a sub-range of diameters and a sub range of heights.

The tubular braid can have two distinct implanted shapes based on the predetermined shape and constrained by the geometry of an aneurysm in which the tubular braid is implanted. In other words, the implant can be implanted in either a larger aneurysm or a smaller aneurysm, the smaller aneurysm having a height measuring less than the height of the larger aneurysm, and the tubular braid can take one of the two implanted shapes when implanted in the larger aneurysm and the tubular braid can take on the other of the implanted shapes when implanted in the smaller aneurysm. In either implanted shape, the first, outer segment of the predetermined shape can be positioned to form an outer layer that juxtaposes/apposes an aneurysm wall and the inversion adjacent to the outer segment in the predetermined shape can be positioned to form a proximal inversion at an aneurysm neck. When implanted in the larger aneurysm, the second, middle segment of the predetermined shape can form a sack that apposes a portion of the aneurysm wall and apposes the outer layer of the braid, the pinched end can be suspended within the sack of the braid, and the open end can encircle the sack. When implanted in the smaller aneurysm, the middle segment of the predetermined shape can be folded to form a middle layer that apposes the outer layer and an inner layer that apposes the middle layer, the open end can be positioned near the fold dividing the middle and inner layers, and the pinched end can be positioned near the proximal inversion and aneurysm neck. The tubular braid in the predetermined shape can have a bend in the middle, second segment, and when tubular braid is in the smaller aneurysm implanted shape, the middle segment can fold at the bend to separate the middle layer from the inner layer.

An example implant having the tubular braid having two distinct implanted shapes can treat aneurysms within a range of sizes including an aneurysm having a diameter of 4 mm and a height of 6 mm, an aneurysm having a diameter of 5 mm and a height of 8 mm, and an aneurysm having a diameter of 6 mm and a height of 6 mm. Additionally, or alternatively, the implant can be suitable for treating aneurysms within a continuum of aneurysm sizes, the continuum bounded by and including aneurysm diameters between 4 mm and 5 mm and heights between 6 mm and 8 mm. The implant capable of treating aneurysms having the aforementioned sizes, when compressed for delivery through a microcatheter can have a length measuring between about 22 mm and about 25 mm.

As an alternative to having two distinct implanted shapes, the implant can have an implanted shape that includes a compaction resistant post extending within an inner sack of the braid and extending between a proximal inversion near an aneurysm neck and a distal inversion near a distal portion of an aneurysm wall. In the implanted shape, the tubular braid can have an outer layer that corresponds to the outer segment in the predetermined shape, the inner sack in the implanted shape can correspond to the middle segment in the predetermined shape, the compaction resistant post can correspond to the inner, third segment in the predetermined shape, and the distal and proximal inversions can correspond to the two inversions in the predetermined shape. The compaction resistant post can serve to inhibit the implant from impacting when implanted in the aneurysm.

An example method of treating an aneurysm can include one or more of the following steps presented in no particular order, and the method can include additional steps not included here. A tubular braid having an open end and a pinched end can be selected and shaped to a predetermined shape. The predetermined shape can be formed by inverting the braid to form a distal inversion, moving the open end over some or all of the braid to form a proximal inversion, shaping a first segment that extends between the open end and the proximal inversion, shaping a second segment that extends between the two inversions, positioning the open end to encircle the second segment, shaping a third segment that extends between the distal inversion and the pinched end of the braid, and positioning the second segment to surround the third segment. Forming the predetermined shape can further include shaping the open end and second segment so that the open end has a diameter greater than or equal to the maximum diameter of the second segment.

The tubular braid can be formed in the predetermined shape such that the tubular braid is implantable in two distinct implanted shapes and in either of two aneurysms having differing heights such that the braid takes on one implanted shape in the taller aneurysm and the second, different implanted shape in the shorter aneurysm. The example method can further include reshaping the tubular braid into one of the two distinct implanted shapes. When the tubular braid is reshaped for the taller aneurysm, the first segment can be reshaped to form an outer braid layer that apposes an aneurysm wall of the taller aneurysm, the proximal inversion can be positioned at the neck of the taller aneurysm, and the second segment can be reshaped to form a sack that nests within the outer layer and also apposes the aneurysm wall of the taller aneurysm. When the tubular braid is reshaped for the shorter aneurysm, the first segment can be reshaped to form an outer braid layer that apposes an aneurysm wall of the shorter aneurysm, the proximal inversion can be positioned at the neck of the shorter aneurysm, and the second segment can be folded to form a middle braid layer that apposes the outer layer and an inner braid layer that apposes the middle layer.

Forming the predetermined shape can further include forming a bend in the second segment, and when the tubular braid is reshaped for the shorter aneurysm, the second segment can be folded at the bend to form the fold that separates the middle braid layer and the inner braid layer.

When the tubular braid is reshaped for the taller aneurysm, the pinched end can be suspended within the sack. When the tubular braid is reshaped for the smaller aneurysm, the pinched end can be positioned near the proximal inversion.

When the tubular braid is reshaped for the taller aneurysm, the open end can encircle the sack. When the tubular braid is reshaped for the shorter aneurysm, the open end can be positioned near the fold separating the middle braid layer and the inner braid layer.

The method can further include shaping the tubular braid into a delivery shape to be delivered through a microcatheter. The tubular braid can have a length in the delivery shape that is measured between the open end and the pinched end. When the tubular braid is shaped to the predetermined shape, it can be shaped to have an outermost diameter. The length of the tubular braid in the delivery shape can measure between 3.5 and 5 times that of the outermost diameter of the tubular braid in the predetermined shape.

In the predetermined shape, the outermost diameter can be shaped to be between 2 and 1/3 times the height of the tubular braid.

When the tubular braid is shaped to the predetermined shape, the tubular braid can be shaped to be suitable to be implanted in an aneurysm having a diameter of 4 mm and a height of 6 mm, an aneurysm having a diameter of 5 mm and a height of 8 mm, and an aneurysm having a diameter of 6 mm and a height of 6 mm. Additionally, or alternatively, when the tubular braid is shaped to the predetermined shape, the tubular braid can be shaped to be suitable for treating a continuum of aneurysm sizes including aneurysms having diameters between 4 mm and 5 mm and heights between 6 mm and 8 mm. The tubular braid that is suitable for treating aneurysms sized as above can be extended to a single layer delivery shape having a length measuring between about 22 mm and about 25 mm, the delivery shape sized to be delivered through a microcatheter.

The method can further include positioning the proximal inversion on a proximal side of a plane defining a boundary between an aneurysm and blood vessel branches. The first segment can be reshaped to appose an aneurysm wall and the second segment can be reshaped to provide an outwardly radial force in the plane. The force can be sufficient to appose the first segment to the aneurysm neck. The force can also be sufficient to resist compaction of the implant within the aneurysm.

The method can further include collapsing the implant to fit within a microcatheter and pushing the pinched end of the unsheathed tubular braid through a majority of the length of the microcatheter to an aneurysm within a patient.

BRIEF DESCRIPTION OF THE DRAWINGS

The above and further aspects of this invention are further discussed with reference to the
following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1A is an illustration of an example implant having a tubular braid in a predetermined shape according to aspects of the present invention;

FIG. 1B is an illustration of the example implant with the tubular braid in a first implanted shape according to aspects of the present invention;

FIG. 1C is an illustration of the example implant with the tubular braid in a second implanted shape according to aspects of the present invention;

FIGS. 2A through 2H are illustrations of an implant having a tubular braid that expands to a predetermined shape similar to as illustrated in FIG. 1A as the tubular braid exits a microcatheter according to aspects of the present invention;

FIGS. 3A through 3H are illustrations of the implant showing the tubular braid expanding to a first implanted shape and a second implanted shape within an aneurysm according to aspects of the present invention;

FIGS. 5A through 5D are illustrations of the example implant as illustrated in FIGS. 1A through 1C implanted in either the first implanted shape or the second implanted shape in aneurysms ranging in size according to aspects of the present invention;

FIGS. 6A and 6B are illustrations of measurements of an example implant and an aneurysm according to aspects of the present invention;

DETAILED DESCRIPTION

Figure 2F:
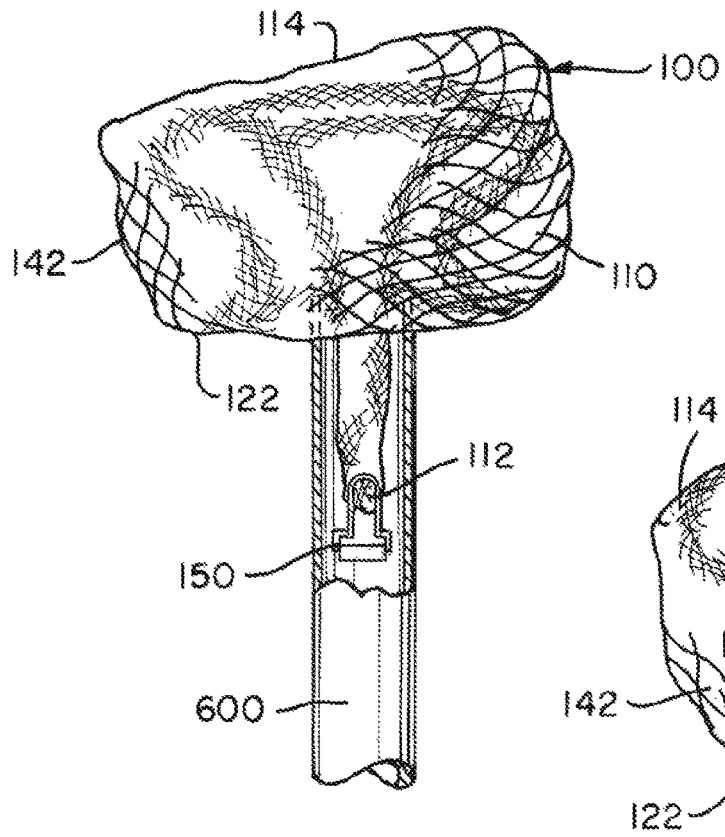

Examples presented herein generally include a braided implant that can secure within an aneurysm sac and occlude a majority of the aneurysm's neck. The implant can include a tubular braid that can be set into a predetermined shape, compressed for delivery through a microcatheter, and implanted in at least one implanted position that is based on the predetermined shape and the geometry of the aneurysm in which the braid is implanted. When compressed, the implant can be sufficiently short to mitigate friction forces produced when the implant is delivered unsheathed through the microcatheter allowing for a more simplistic delivery system compared to some other known braided embolic implant delivery systems FIGS. 1A through 1C are illustrations of an example braided implant 100 that can have a predetermined shape as illustrated in FIG. 1A and two distinct implanted shapes as illustrated in FIGS. 1B and 1C. The implant 100 can treat a range of aneurysm sizes including a larger aneurysm 10a as illustrated in FIG. 1B and a smaller aneurysm 10b as illustrated in FIG. 1C. The implant 100 can have a first implanted shape (FIG. 1B) that can be conducive for treating larger aneurysms 10a and a second implanted shape (FIG. 1C) that can be conducive for treating smaller aneurysms 10b. The implant 100 can include a tubular braid 110 having an open end 114 and a pinched end 112. The implant 100 can include a detachment feature 150 attached to the braid 110 at the pinched end 112. The tubular braid 110 can be formed in the predetermined shape (FIG. 1A), collapsed for delivery through a microcatheter, attached to a delivery system at the detachment feature 150, and implanted in a shape similar to one or the other of the two implanted shapes (FIG. 1B or FIG. 1C).

Referring to FIG. 1A, when in the predetermined shape, the tubular braid 110 can include two inversions 122, 124, dividing the braid 110 into three segments 142, 144, 146. In the predetermined shape, the braid 110 can have an outer segment 142 extending from the open end 114 of the braid 110 to one of the inversions 122, an inner segment 146 extending from the pinched end 112 of the braid 110 to the other of the inversions 124, and a middle segment 144 extending between the two inversions 122, 124. When in the predetermined shape, the tubular braid 110 can be substantially radially symmetrical about a central vertical axis y (see FIG. 6A). FIG. 1A illustrates a profile of each segment 142, 144, 146, and the detachment feature 150 is illustrated as a flat key that can be used with a mechanical implant delivery system (not illustrated).

The tubular braid 110 can be formed into the predetermined shape by first inverting the braid outwardly to separate the inner segment 146 from the middle segment 144 with an inversion 124, then the middle segment 144 can be shaped over a form to produce the substantially "S" shaped profile illustrated, and finally, the braid 110 can be inverted outwardly again to separate the middle segment 144 from the outer segment 142 with another inversion 122. If necessary, the braid can be trimmed at the open end 114. The open end 114 can be positioned to encircle the middle segment 144. The open end 114 can positioned within the middle third section of the braid's height as illustrated.

It can be advantageous to minimize a neck opening 126 defined by the lower extension of the "S" shape of the middle segment 144 to maximize occlusion of an aneurysm neck when the implant 100 is implanted. The middle segment 144 can have one or more bends 132, 134. The bends 132, 134 can be positioned facilitate the movement of the braid 110 into the second implanted shape illustrated in FIG. 1C and the bends 132, 134 can be positioned to stabilize the braid 110 in the first and/or second implanted shape.

The tubular braid 110 can include memory shape material that can be heat set to a predetermined shape, can be deformed for delivery through a catheter, and can self-expand to an implanted shape that is based on the predetermined shape and confined by the anatomy of the aneurysm in which it is implanted.

As illustrated in FIG. 1B, when in the first implanted shape, the braid 110 can have an outer layer 142a contacting the aneurysm's wall 14a, a sack 144a nested within the outer layer 142a, a proximal inversion 122a positioned at the aneurysm's neck 16a, and a distal inversion 124a positioned near a distal portion 15a of the aneurysm wall 14a. In the first implanted shape, the detachment feature 150 and pinched end 112 of the braid 110 can be suspended within the sack 144a.

As illustrated in FIGS. 1A and 1B, the tubular braid 110 in the first implanted shape can be radially compressed and vertically extended compared to the predetermined shape. The outer layer 142a in the first implanted shape can correspond to the outer layer 142 in the predetermined shape, the proximal inversion 122a in the first implanted shape can correspond to the inversion 122 adjacent to the outer layer 142 in the predetermined shape, the sack 144a in the first implanted shape can correspond to the middle segment 144 in the predetermined shape, the distal inversion 124a in the first implanted shape can correspond to the inversion 124 adjacent to the inner segment 146 in the predetermined shape, and an inner braid segment 146a suspending the detachment feature 150 in the first implanted shape can correspond to the inner segment 146 in the predetermined shape. In the first implanted shape, the sack 144a can have a neck opening 126a corresponding to the neck opening 126 in the predetermined shape.

As illustrated in FIG. 1C, when in the second implanted shape, the braid 110 can have an outer layer 142b contacting the aneurysm's wall 14b, a proximal inversion 122b positioned at the aneurysm's neck 16b, a middle layer 144b extending within the outer layer 142b and pressing against the outer layer 142b, a distal inversion 124b positioned near the open end 114 of the braid 110, and an inner layer 146b extending within the middle layer 144b and pressing against the middle layer 144b. In the second implanted shape, the detachment feature 150 and pinched end 112 of the braid 110 can be positioned at the aneurysm neck 16b, near the proximal inversion 122b.

As illustrated in FIGS. 1A and 1C, the tubular braid 110 in the second implanted shape can be radially compressed compared to the predetermined shape, and the middle segment 144 of the predetermined shape can be folded so that the height of the tubular braid 110 is compressed in the second implanted shape compared to the predetermined shape. Alternatively, when implanted in the second implanted shape in aneurysms having a diameter that is significantly smaller than the aneurysm's height, the second implanted shape can be radially compressed compared to the predetermined shape and the height of the braid in the second implanted shape can be greater than the height of the braid in the predetermined shape.

The outer layer 142b in the second implanted shape can correspond to the outer layer 142 in the predetermined shape, the proximal inversion 122b in the second implanted shape can correspond to the inversion 122 adjacent to the outer layer 142 in the predetermined shape, the middle layer 144b and inner layer 146b in the second implanted shape can correspond to the middle segment 144 in the predetermined shape, the distal inversion 124b in the second implanted shape can correspond to a bend 134 in the middle segment 144 in the predetermined shape, and a portion of the braid 110 near the detachment feature 150 forming the inner layer 146b in the second implanted shape can correspond to the inner segment 146 in the predetermined shape.

FIGS. 2A through 2H are illustrations of an example implant 100 having a braid 110 expanding to a predetermined shape as the braid 110 exits a microcatheter 600. The implant 100 has a predetermined shape similar to as illustrated in FIG. 1A. As illustrated in FIG. 2A, the braid 110 can be shaped to a delivery shape that is extended to a single layer of tubular braid having a compressed circumference/diameter sized to be delivered through the microcatheter 600 and a length L. The illustrated implant 100 has a length L of between about 22 mm and about 25 mm. As will be appreciated and understood by a person of ordinary skill in the art, the length L of a specific braid 110 can be tailored based on the size and shape of the aneurysm being treated.

During delivery through the microcatheter 600, the detachment feature 150 can be attached to a delivery system at a proximal end of the implant 100, the pinched end 112 can be positioned near the proximal end of the implant 100, and the open end 114 can define the distal end of the implant 100. Collapsing the braid 110 to a single layer tube can result in a braid 110 that has a sufficiently small diameter and a sufficiently short length L to mitigate effects of friction force on the braid 110 when it is delivered through the microcatheter, allowing the braid 110 to be delivered unsheathed in some applications.

As illustrated in FIG. 2B, the open end 114 can be positioned to exit the microcatheter 600 before any other portion of the braid 110 exits the microcatheter. The open end 114 can expand as it exits the microcatheter 600. If the open end 114 is unconstrained by an aneurysm as illustrated, the open end can expand to its circumference in the predetermined shape.

As illustrated in FIG. 2C, the distal portion of the braid 110 can continue to expand radially as it exits the microcatheter 600.

As illustrated in FIG. 2D, the braid 110 can form the inversion 122 defining the outer segment 142 as the braid 110 is further pushed out of the microcatheter 600.

Figure 2G:
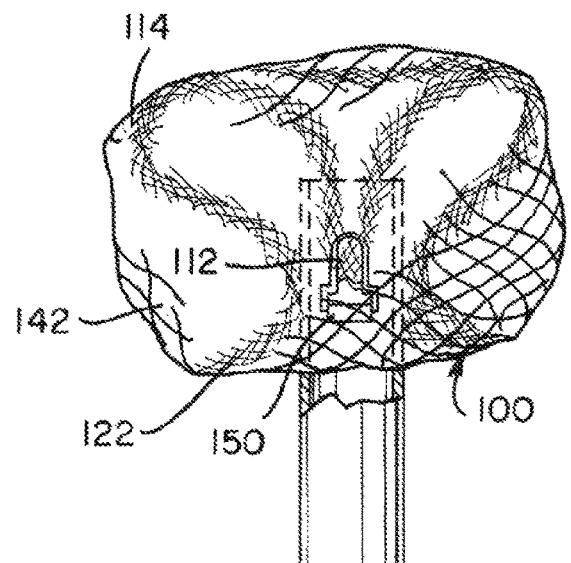

As illustrated in FIGS. 2E through 2G, the "S" shape of the middle segment 144 can begin to form as the braid 110 is further pushed from the microcatheter 600.

Figure 2H:
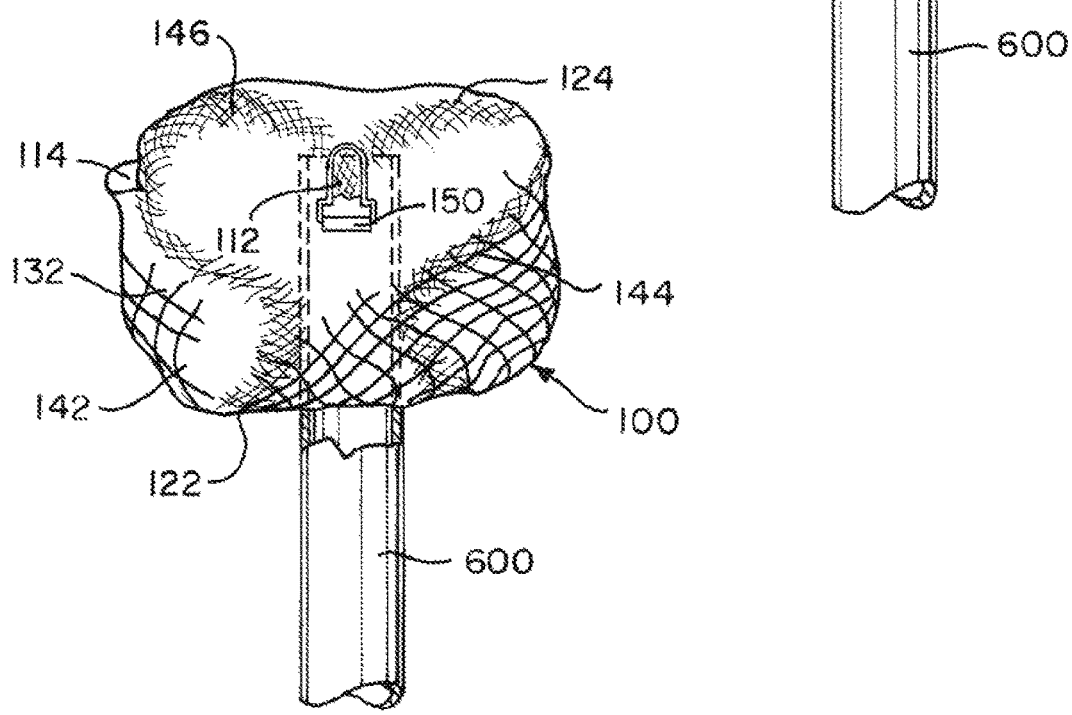

As illustrated in FIG. 2H, when all, or nearly all of the braid 110 exits the microcatheter 600, the braid 110, not confined by an aneurysm, can expand to a predetermined shape similar to the shape illustrated in FIG. 1A. In the predetermined shape, the braid 110 of the illustrated implant has a diameter between about 6 mm and about 6.5 mm and a height between about 5 mm and about 5.5 mm.

The ratio of the outermost diameter of the braid 110 in the predetermined shape illustrated in FIG. 2H to the length of the braid 110 in the delivery shape illustrated in FIG. 2A is between about 0.3 and about 0.24.

FIGS. 3A through 3H are illustrations of the implant 100 illustrated in FIGS. 2A through 2H expanding within an aneurysm 10 in two different implanted shapes. The aneurysm 10 has a height of about 6 mm, a diameter of about 6 mm, and a neck diameter of about 4 mm. Comparing the dimensions of the aneurysm 10 to the braid 110 in the predetermined shape illustrated in FIG. 2H, the braid 110 has a slightly larger diameter and a slightly smaller height, and the interior of the aneurysm 10 is substantially spherical while the outer dimensions of the braid 110 are more cylindrical (see FIGS. 6A and 6B for measurement orientation). When the braid 110 of the implant 100 is confined by the aneurysm 10, the braid 110 is therefore be radially constrained.

Figure 3B:
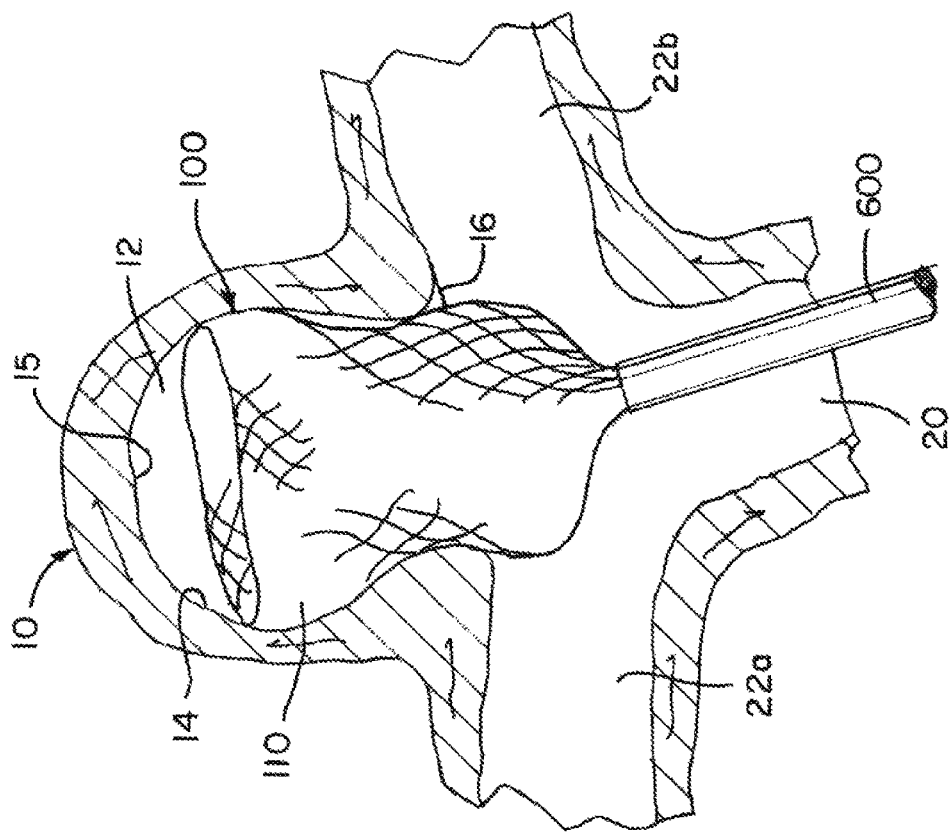
Figure 3A:
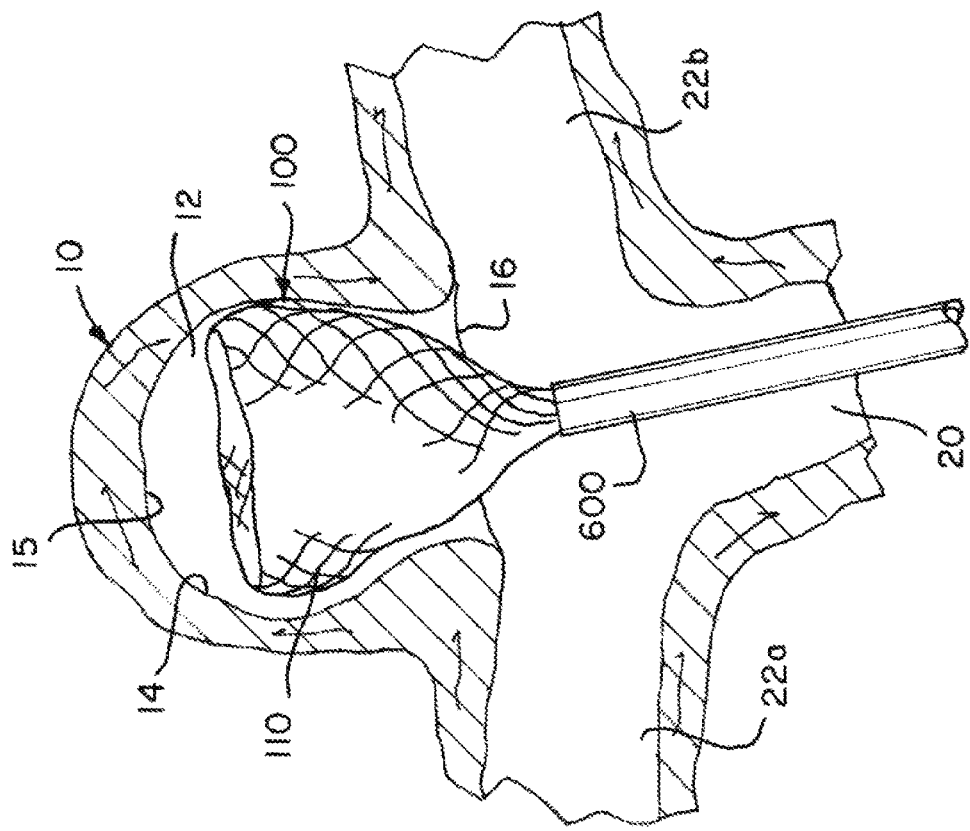

As illustrated in FIG. 3A, the implant 100 can be delivered to the aneurysm 10 through the microcatheter 600, as described in relation to FIG. 2A. The open end 114 of the tubular braid 110 can expand within the aneurysm 10 as it exits the microcatheter 600. The illustrated aneurysm 10 is positioned at a bifurcation including a stem blood vessel 20 and two branch vessels 22a, 22b, and the microcatheter 600 is illustrated being delivered through the stem blood vessel 20. It is contemplated that the implant could be delivered to an aneurysm on a sidewall of a blood vessel through a curved microcatheter, and such a procedure is intended to be embraced by the scope of the present disclosure.

As illustrated in FIG. 3B, as the braid 110 is further pushed distally from the microcatheter 600, the braid 110 can expand to appose the aneurysm wall 14 and conform to the aneurysm neck 16. The aneurysm 10 being treated can have a diameter that is less than the outer diameter of the tubular braid 110 in the predetermined shape so that the braid 110 tends to expand outwardly, providing a force against the aneurysm wall 14, and sealing around the perimeter of the aneurysm neck 16. The implant 100 can be particularly suitable for treating a wide neck aneurysm such as commonly occur at bifurcations because the radial force provided by the braid 110 against the aneurysm wall 14 and perimeter of the neck 16 can be sufficient to both anchor the implant 100 in a wide neck aneurysm and seal the neck 16 of the aneurysm 10.

Figure 3C:
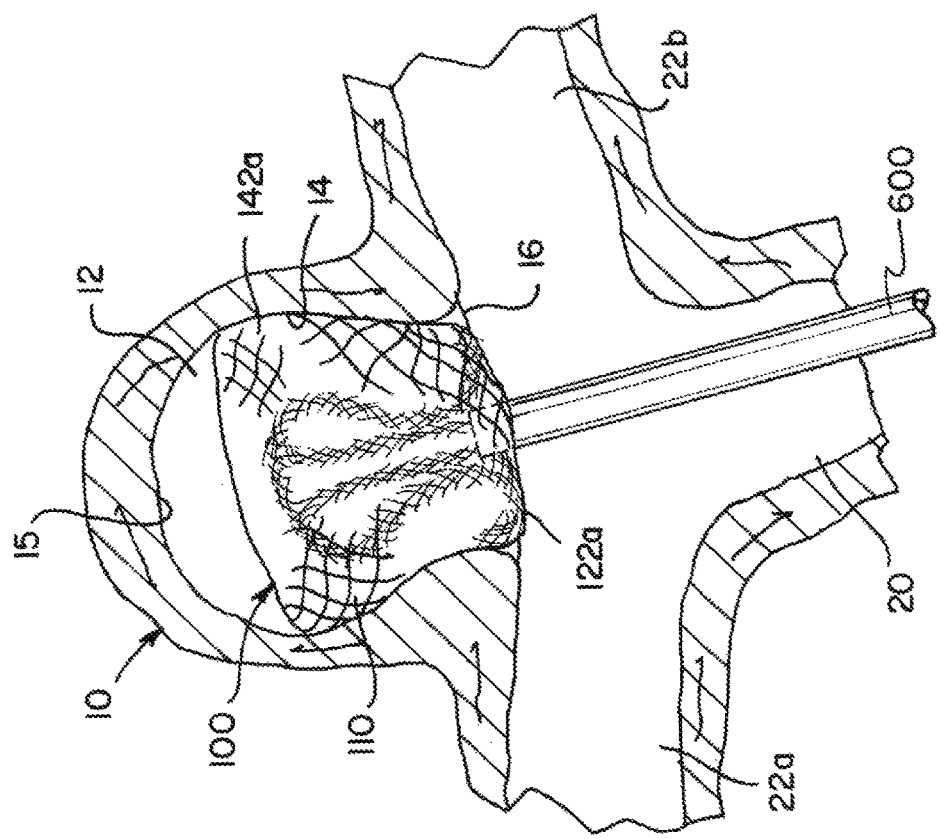

As illustrated in FIG. 3C, as the braid 110 is further pushed distally from the microcatheter 600, the proximal inversion 122a can be formed.

Figure 3D:
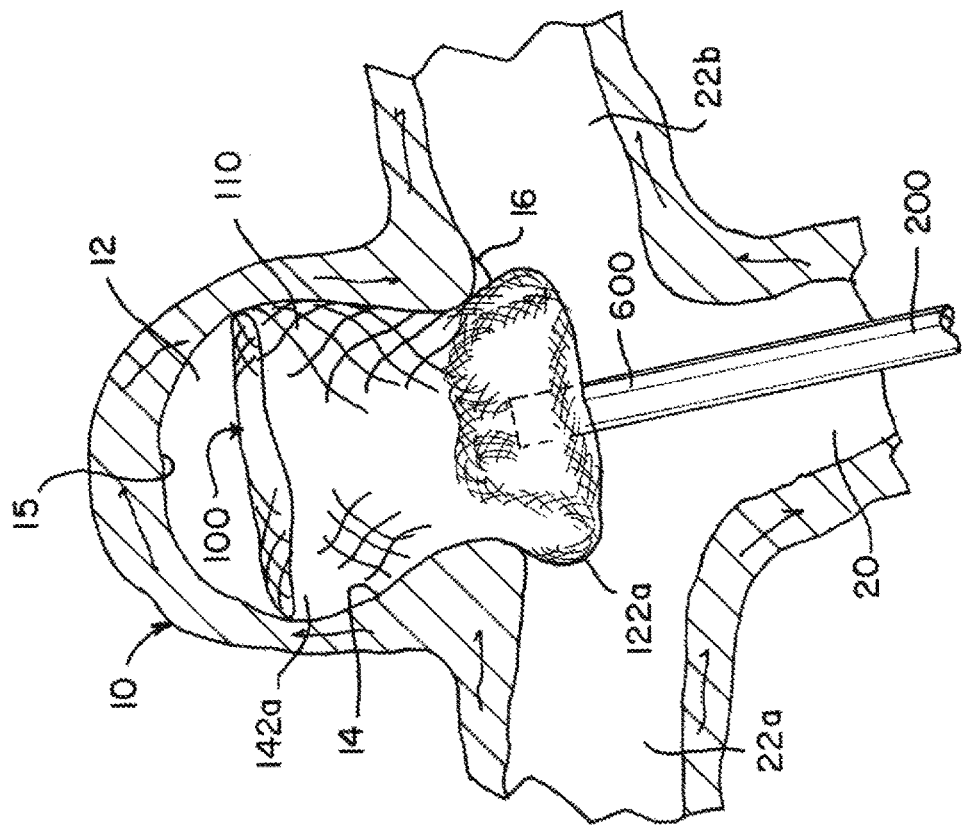

As illustrated in FIG. 3D, the microcatheter 600 can be manipulated to place the proximal inversion 122a at the aneurysm neck 16. The proximal inversion 122a can be placed on a proximal side of a plane defining a boundary 18 (See FIG. 6B) between the aneurysm 10 and the branch vessels 22a, 22b. In some applications it can be advantageous to place the proximal inversion 122a far enough in the proximal direction from the plane 18 so that the outer layer 142a of the braid 110 seals around the outer perimeter of the aneurysm neck 16, but not so far proximally that the implant 100 becomes an obstruction to the blood vessels 22a, 22b, 20.

As illustrated in FIG. 3E, the braid 110 can expand within the aneurysm sac 12 and extend to appose an inner surface of the outer layer 142a of the braid 110. The apposition to the outer layer 142a can provide additional force to anchor the outer layer 142a to the aneurysm wall 14.

As illustrated in FIG. 3F, the aneurysm 10 has a height that can accommodate the tubular braid 110 in the first implanted shape similar to that illustrated in FIG. 1B. Because the braid 110 is radially constrained and has a more cylindrical shape compared to the substantially spherical shape of the aneurysm, the braid 110 can extend beyond the height of the predetermined shape to accommodate aneurysms taller than the predetermined shape. In the illustration, the tubular braid 110 of the implant 100 in the predetermined shape has a height between about 0.5 mm and 1 mm less than the height of the aneurysm, or in other words, the implant has extended between about 10% and about 20% in height in the first implanted shape compared to the predetermined shape.

The braid can be pulled proximally as illustrated in FIG. 3G to form a second implanted shape as illustrated in FIG. 3H that is similar to the second implanted shape illustrated in FIG. 1C, but different in that the aneurysm 10b illustrated in FIG. 1C is smaller (proportionally compared to the braid 110) than the mock aneurysm 10 illustrated in FIG. 3H. Before the implant 100 is released from the delivery system, the implant 100 can be partially or fully retracted into the microcatheter 600 and repositioned in either of the first implanted shape or the second implanted shape. Additionally, or alternatively, the microcatheter 600 can be moved distally to move the braid 110 from the second implanted shape illustrated in FIG. 3H to the first implanted shape illustrated in FIG. 3F. In some applications, while positioning the implant 100, a physician can choose whether the first implanted shape or the second implanted shape is more suitable for the anatomy of the aneurysm and treatment site. For treatments involving aneurysms and implants shaped similar to the aneurysm 10 and implant 100 illustrated in FIGS. 3A through 3H, it can be more advantageous to shape the braid 110 in the first implanted shape as illustrated in FIG. 3F (rather than the second implanted shape illustrated in FIG. 3G) because the first implanted shape in this example implementation provides a larger surface area of the braid 110 in contact with the aneurysm wall 14.

Figure 4B:
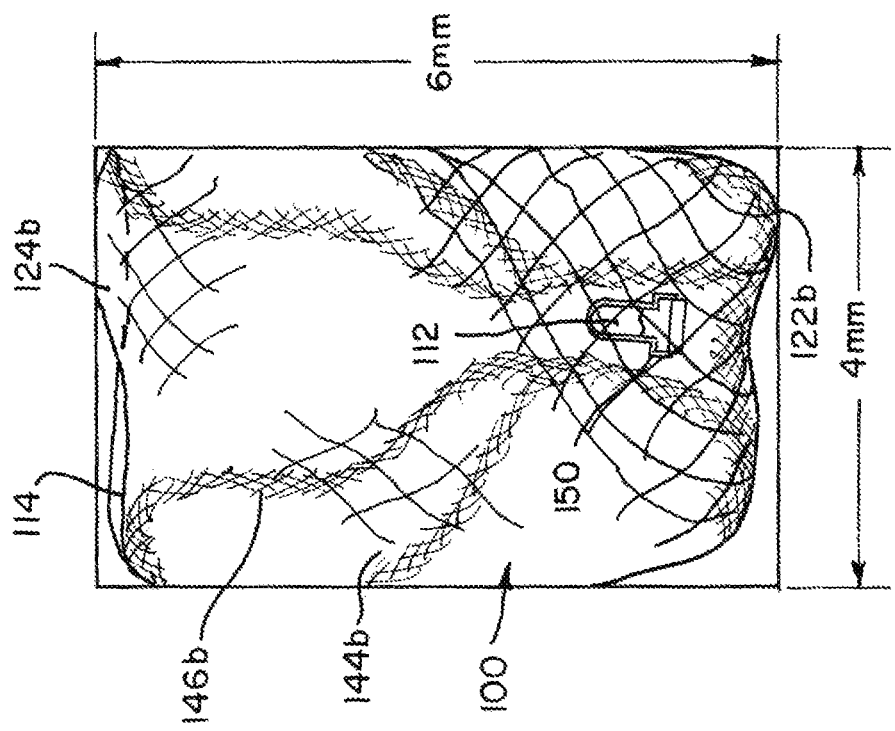
FIG. 4B is an illustration of the implant showing the tubular braid expanded in the second implanted shape in a tube having a 4 mm diameter according to aspects of the present invention.
Figure 4A:
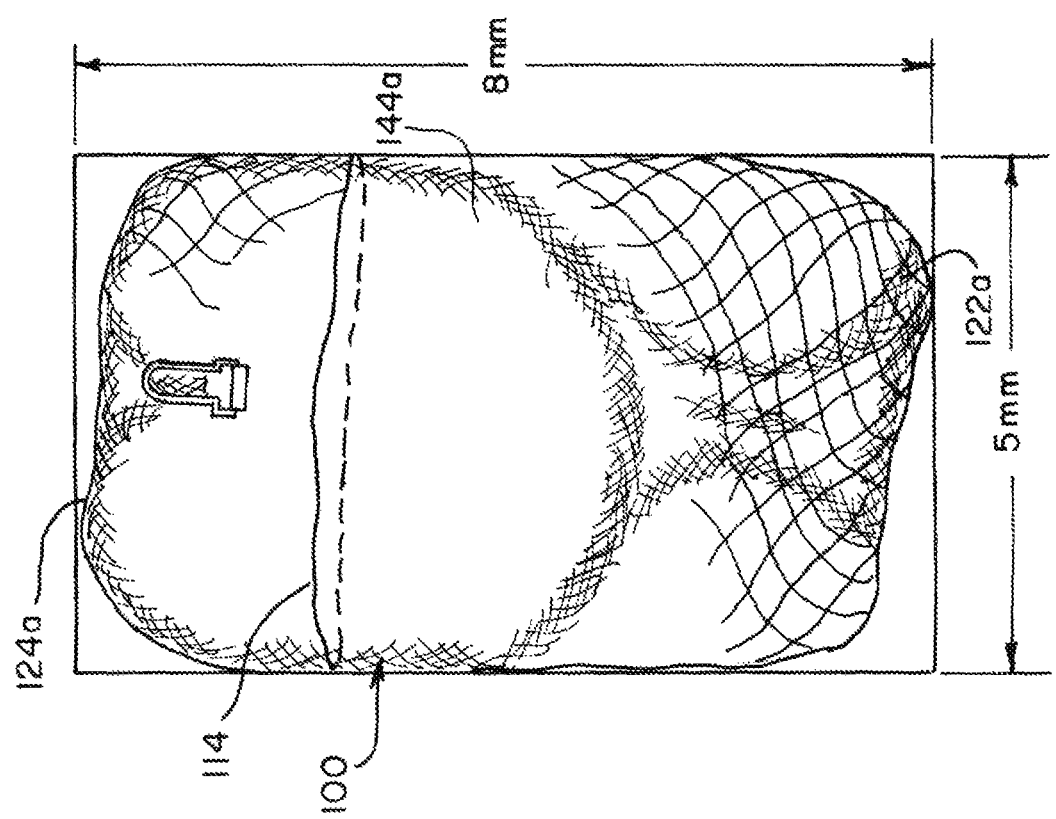
FIG. 4A is an illustration of the implant showing the tubular braid expanded in the first implanted shape in a tube having a 5 mm diameter according to aspects of the present invention.

FIGS. 4A and 4B are illustrations of the braid 110 of the example implant illustrated in FIGS. 2A through 2H and 3A through 3H showing the tubular braid 110 expanded within tubes to determine a range of aneurysm diameters and aneurysm heights that an implant 100 having the dimensions of the example implant 100 would be suitable for treating. FIG. 4A illustrates the braid 110 in a tube having a 5 mm diameter. The braid 110 is in the first implanted shape and has a height of about 8 mm. The braid 110 is therefore radially constrained from its predetermined shape by between about 1 mm and 1.5 mm in diameter, or between about 17% and 23%, and expanded vertically in height by between about 2.5 mm and 3 mm, or between about 45% and 60%.

FIG. 4B illustrates the braid 110 in a tube having a 4 mm diameter. The braid 110 is in the second implanted shape and has a height of about 6 mm. The braid is therefore radially constrained from its predetermined shape by between about 2 mm and 2.5 mm in diameter, or between about 33% and 38%, and expanded vertically between about 0.5 mm and 1 mm, or between about 10% and 20%.

Implants having a predetermined shape and dimensions as illustrated and described in relation to FIG. 2H can therefore be suitable for treating aneurysms having a diameter between and including about 4 mm and about 5 mm and a height between and including about 6 mm and about 8 mm. As illustrated in FIG. 3F, the implant can also be suitable for treating an aneurysm having a diameter of 6 mm and a height of 6 mm. As will be appreciated and understood by a person of ordinary skill in the art, the dimensions of the tubular braid in the predetermined shape can be tailored to treat aneurysms within a range of sizes not specifically outlined herein according to the principles described herein. It is contemplated that a collection of implants so shaped can be made available to physicians, and a physician can choose a suitable implant from the collection based on aneurysm height, diameter, neck diameter, and/or other anatomical features.

A collection of implants, each having a uniquely shaped tubular braid can be created to provide a catalogue of implants for treating aneurysms ranging in diameter and height. The catalogue can include implants suitable for treating aneurysms ranging from 3 mm to 15 mm in diameter and ranging from 3 mm to 15 mm in height, or in another example, ranging from 3 to 11 mm in diameter and 3 to 7 mm in height. As will be apricated and understood by a person of ordinary skill in the art, some aneurysm dimensions are extremely rare, and the catalog need not include implants for treating aneurysms having a large height: diameter ratio or a large diameter:height ratio.

Each implant in the collection can be suitable for treating aneurysms with a sub range of diameters and a sub-range of heights. An example catalogue can include a listing of implants for treating aneurysms of one or more of, but not limited to, the following size sub ranges (diameter range in mm, height range in mm): (3-5, 3-5), (6-8, 4-5), and (9-11, 5-7).

In some examples, each size sub range can be treated by a single implant having a tubular braid uniquely sized and shaped to be suitable for treating aneurysms within that sub range. In some examples, the sub ranges in the catalogue can be represented by implants each having a tubular braid with a delivery length (length when the braid is collapsed for delivery through a microcatheter) that is about 10 mm, about 40 mm, and/or including a length in between.

As will be appreciated and understood by a person of ordinary skill in the art, aneurysm height and diameter are measured with some margin of error. To that end, the size sub range included in the catalogue for a given implant can represent a portion of aneurysm sizes that can be treated with the implant and the implant can treat aneurysms outside of the listed sub range. For instance, an implant listed for treating aneurysms having heights between height a and height b and diameter range between diameter x and diameter y can be suitable for treating aneurysms slightly taller than the maximum listed height b if the diameter of the aneurysm is near the lower limit of the range (about diameter x), the implant can be suitable for treating diameters slightly larger than diameter y if the height of the aneurysm is near the lower limit of the height range (about height a).

FIGS. 5A through 5D are illustrations of the example implant 100 as illustrated in FIGS. 1A through 1C implanted in either the first implanted shape or the second implanted shape in aneurysms ranging in size. FIG. 5A illustrates a large aneurysm 10a, FIGS. 5B and 5C illustrate a medium aneurysm 10c, and FIG. 5D illustrates a small aneurysm 10b. The implant 100 is advantageously implanted in an aneurysm 10a, 10b, 10c having a diameter about equal to or smaller than the diameter of the braid 110 in the predetermined shape so that the braid 110 provides an outward force F against the aneurysm wall 14 when implanted. The braid 110 can have inner layers that press against one or more outer layers, contributing to the force F.

As illustrated in FIG. 5A, the maximum size of an aneurysm 10a that the implant 100 can be suitable for treating can be determined by the dimensions that the braid 110 can take in the first implanted shape. The pinched end 112 and detachment feature 150 can be positioned near a distal portion 15a of the aneurysm wall 14a as similarly illustrated in FIG. 1B.

As illustrated in FIG. 5B, the implant 100 can also be suitable for treating a medium sized aneurysm 10c that is smaller than the aneurysm 10a illustrated in FIG. 5A in the first implanted shape. To fit within the medium aneurysm 10c in the first implanted shape, the pinched end 112 and detachment feature 150 can be positioned away from the distal portion 15c of the aneurysm wall compared to the position of the pinched end 112 and detachment feature 150 in the large aneurysm 10a. In the predetermined shape (see FIG. 1A), the middle segment 144 can include a bend 134 to stabilize the tubular braid 110 in the first implanted shape in the medium aneurysm 10c as illustrated in FIG. 5B.

As illustrated in FIG. 5C, the implant 100 can also be suitable for treating the medium sized aneurysm 10c in the second implanted shape. The middle segment 144 of the braid in the predetermined shape (see FIG. 1A) can be folded to form a middle layer 144b and an inner layer 146b similar to as described in relation to FIG. 1C. In some applications, either implanted shape could be effective for treating the aneurysm 10c, and a physician can select a preferred shape during treatment. For instance, a physician can decide to use the first implanted shape (FIG. 5B) to elongate the implant so that the proximal fold 122a can be placed proximally outside of the aneurysm neck, or the physician can decide to use the second implanted shape (FIG. 5C) to provide more layers of braid at the aneurysm neck to occlude the neck opening 16c.

As illustrated in FIG. 5D, the minimum size of aneurysm 10b that the implant 100 can be suitable for treating can be determined by the dimensions that the braid 110 can take in the second implanted shape. The open end 114 and/or the distal fold 124b can be collapsed near a distal portion 15b of the aneurysm wall in the second implanted shape.

FIG. 6A is an illustration of height HI and diameter D1, D2 measurements of an example implant 100 in a predetermined shape. In the predetermined shape, the braid 110 of the example implant 100 can be substantially radially symmetrical about vertical axis y, and therefore can have substantially circular concentric cross-sections each describable by its diameter. FIG. 6A highlights the height HI of the implant 100 in a predetermined shape measured between the inversions 122, 124, the outer diameter D1 of the outer segment 142, which corresponds to the diameter of the open end 114, and the outer diameter D2 of the middle segment D2. Although FIG. 6A illustrates only one example predetermined shape, it should be understood that the height and diameter of example implants described herein 100, 200, 300, 400 and portions thereof can be measured similarly to as illustrated in FIG. 6A.

FIG. 6B is an illustration of height HA, sac diameter DA, and neck diameter DN measurements of an aneurysm 10. The location of the plane 18 defining a boundary between the aneurysm 10 and blood vessels is also illustrated.

Figure 7A:
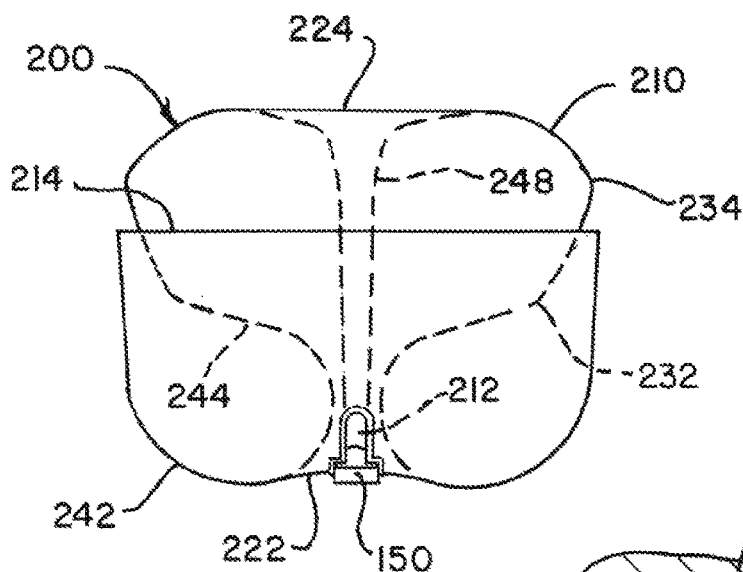
FIG. 7A is an illustration of an example implant having a tubular braid in an alternative predetermined shape according to aspects of the present invention.
Figure 7B:
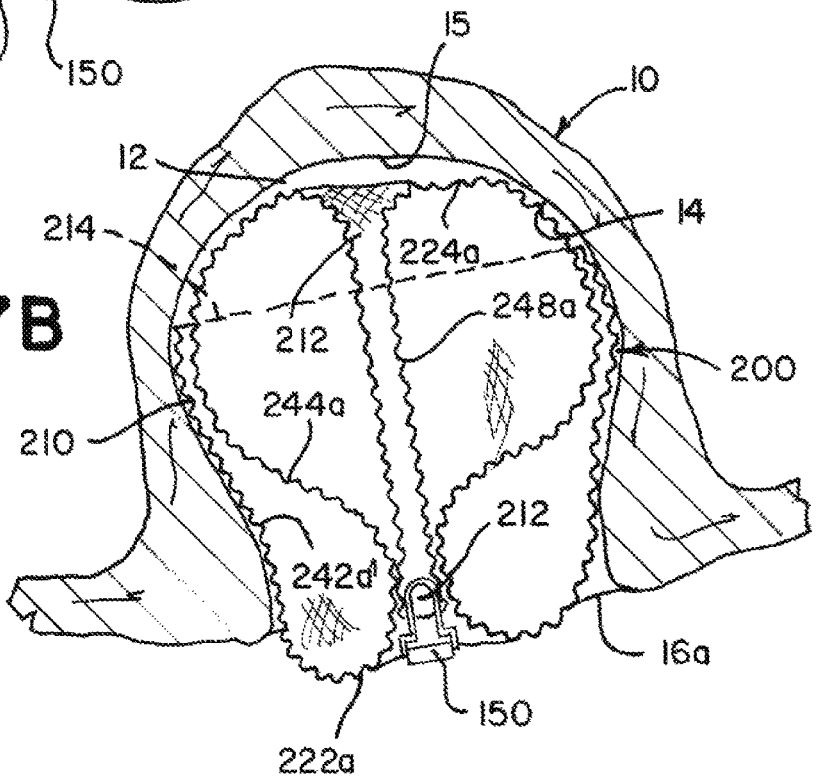
FIG. 7B is an illustration of the example implant illustrated in FIG. 7A with the tubular braid in an implanted shape according to aspects of the present invention.

FIG. 7A is an illustration of an example implant 200 having a tubular braid 210 in an alternative predetermined shape. FIG. 7B is an illustration of the example implant 200 in an aneurysm 10 with the tubular braid 210 in an implanted shape. The tubular braid 210 can have an open end 214 and a pinched end 212. The implant 200 can include a detachment feature 150 attached to the braid 210 at the pinched end 212. The braid 210 can be formed in the predetermined shape, collapsed for delivery through a microcatheter, attached to a delivery system at the detachment feature 150, and implanted in the implanted shape.

As illustrated in FIG. 7A, when in the predetermined shape, the tubular braid 210 can include two inversions 222, 224, dividing the braid 210 into three segments 242, 244, 248. In the predetermined shape, the braid 210 can have an outer segment 242 extending from the open end 214 of the braid 210 to one of the inversions 222, an inner segment 248 extending from the pinched end 212 of the braid 210 to the other of the inversions 224, and a middle segment 244 extending between the two inversions 222, 224. When in the predetermined shape, the tubular braid 210 can be substantially radially symmetrical about a central vertical axis y (see FIG. 6A). FIG. 7A illustrates a profile of each segment 242, 244, 248.

Comparing the predetermined shape of the braid 210 illustrated in FIG. 7A to that of the braid 110 illustrated in FIG. 1A, the outer segments 142, 242 and middle segments 144, 244 are respectively similar to each other, and the inner segment 248 of the braid 210 illustrated in FIG. 7A is longer than the inner segment 146 of the braid 110 illustrated in FIG. 1A. The pinched end 212 of the braid 210 in FIG. 7A is positioned near the inversion 222 adjacent the outer segment 242 rather than near the inversion 124 near the inner segment 146 as illustrated in FIG. 1A. The elongated inner segment 248 illustrated in FIG. 7A can be positioned to help the implant 200 resist compaction when implanted as illustrated in FIG. 7B.

The tubular braid 210 illustrated in FIG. 7A can be formed into the predetermined shape similar to as described in relation to FIG. 1A with some differences. The middle segment 244 need not have bends 132, 134 positioned facilitate the movement of the braid 210 into a second implanted shape. The inner segment 248 as illustrated in FIG. 7A can be made longer than that illustrated in FIG. 1A. The inner segment 248 can be shaped to have a length that is optimized to reduce the likelihood that the implant 200 can become compacted when implanted.

An implant 200 having a braid 210 having a predetermined shape as illustrated in FIG. 7A can have outer dimensions in the predetermined shape including an outer diameter and height similar to as illustrated and described in relation to FIG. 2H. The inner segment 248 of the braid 210 illustrated in FIG. 7A can have a height that is approximately equal to the height of the braid 210 in the predetermined shape.

The braid 210 can be elongated to a single layer tubular braid in a delivery shape that is sized to traverse a microcatheter. The length of the braid 210 in the delivery shape can be measured from the open end 214 to the pinched end 212. A braid 210 having a predetermined shape as illustrated in FIG. 7A and outer dimensions as illustrated and described in relation to FIG. 2H can have a length in the delivery shape that is longer compared to the length of the braid 110 illustrated in FIG. 2A. The length of the braid 210 illustrated in FIG. 7A when in the delivery shape can be longer than a braid 110 having a predetermined shape as illustrated in FIG. 1A by about the height of the braid 110, 210 in the predetermined shape. In other words, an implant 200 having a braid 210 with a predetermined shape as illustrated in FIG. 7A can have an outer diameter between about 6 mm and about 6.5 mm and a height between about 5 mm and 5.5 mm when in the predetermined shape and can be elongated to a single layer tube having a circumference collapsed to fit within a microcatheter and a length measuring between about 27 mm and 30 mm. The ratio of outermost diameter in the predetermined shape to length in the delivery shape can be between about 0.24 and about 0.2.

As illustrated in FIG. 7B, when in the implanted shape, the braid 210 can have an outer layer 242a contacting the aneurysm's wall 14, a sack 244a nested within the outer layer 242a, a proximal inversion 222a positioned at the aneurysm's neck 16, and a distal inversion 224a positioned near a distal portion 15 of the aneurysm wall 14. The detachment feature 150 and pinched end 212 of the braid 210 can be positioned near the aneurysm neck 16, near the proximal inversion 222a. The detachment feature 150 and pinched end 212 can be positioned to reduce the likelihood that the implant 200 becomes impacted.

Figure 8A:
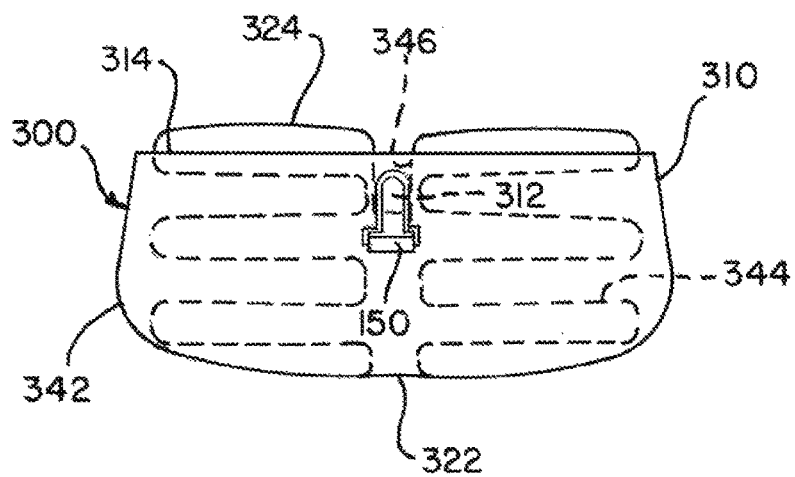
FIG. 8A is an illustration of an example implant having a tubular braid in another alternative predetermined shape according to aspects of the present invention.
Figure 8B:
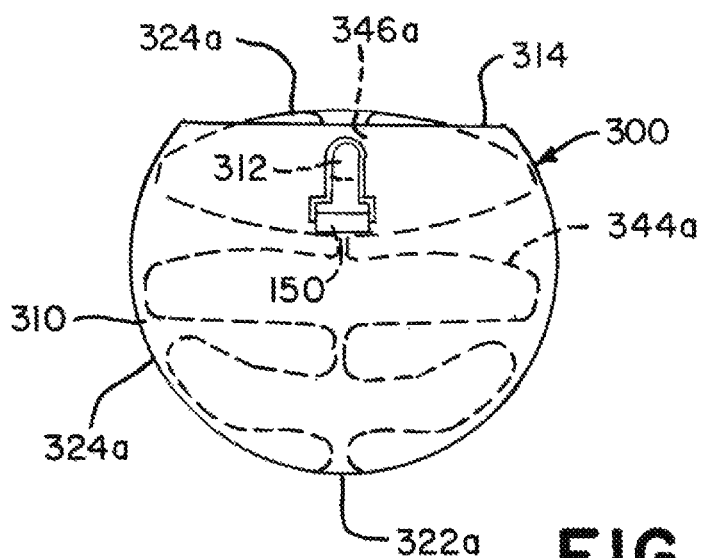
FIG. 8B is an illustration of the example implant illustrated in FIG. 8A with the tubular braid in an implanted shape according to aspects of the present invention.

FIG. 8A is an illustration of an example implant 300 having a tubular braid 310 in another alternative predetermined shape. FIG. 8B is an illustration of the example implant 300 when the tubular braid 310 in an implanted shape. The tubular braid 310 can have an open end 314 and a pinched end 312, and a detachment feature 150 can be attached to the braid 310 at the pinched end 312. The braid 310 can be formed in the predetermined shape, collapsed for delivery through a microcatheter, attached to a delivery system at the detachment feature 150, and implanted in the implanted shape.

As illustrated in FIG. 8A, when in the predetermined shape, the tubular braid 310 can include two inversions 322, 324, dividing the braid 310 into three segments 342, 344, 346. In the predetermined shape, the braid 310 can have an outer segment 342 extending from the open end 314 of the braid 310 to one of the inversions 322, an inner segment 346 extending from the pinched end 312 of the braid 310 to the other of the inversions 324, and a middle segment 344 extending between the two inversions 322, 324. When in the predetermined shape, the tubular braid 310 can be substantially radially symmetrical about a central vertical axis. FIG. 8A illustrates a profile of each segment 342, 344, 346.

Comparing the predetermined shape of the braid 310 illustrated in FIG. 8A to that of the braid 110 illustrated in FIG. 1A, the outer segments 142, 342 and inner segments 146, 346 are respectively similar to each other, and the middle segment 344 of the braid 310 illustrated in FIG. 8A has an undulating pattern rather than the "S" shape of the middle segment 144 of the braid 110 illustrated in FIG. 1A. The undulating middle segment 344 can be radially symmetrical to form a honeycomb shape. When implanted, the middle segment 344 in the undulating pattern can provide a force pattern pressing outwardly to anchor the implant 300 within an aneurysm that is different from a force pattern that could be provided by the middle segment 144 having the "S" shape illustrated in FIG. 1A. The pinched end 312 of the braid 310 in FIG. 8A can be positioned near the inversion 324 adjacent the inner segment 346 as illustrated. Alternatively, the inner segment 346 can be shaped to extend to the inversion 322 adjacent the outer segment 342 to provide a compaction resistant column.

The tubular braid 310 illustrated in FIG. 8A can be formed into the predetermined shape similar to as described in relation to FIG. 1A with some differences. The middle segment 344 can be formed to have an undulating pattern rather than an "S" shaped pattern. The middle segment 344 need not have bends positioned facilitate the movement of the braid 310 into a second implanted shape.

As illustrated in FIG. 8B, when in the implanted shape, the braid 310 can have an outer layer 342a shaped to contact an aneurysm wall, compressed extensions of an undulating middle layer 344a nested within the outer layer 342a, a proximal inversion 322a positioned to be placed an aneurysm neck, and a distal inversion 324a positioned to be placed near a distal portion of the aneurysm wall. The detachment feature 150 and pinched end 312 of the braid 310 can be positioned within the aneurysm sac, either near the distal inversion 324a as illustrated, near the proximal inversion 322a, or at a position in between. The detachment feature 150 and pinched end 312 can be positioned to reduce the likelihood that the implant 300 becomes impacted.

Figure 9A:
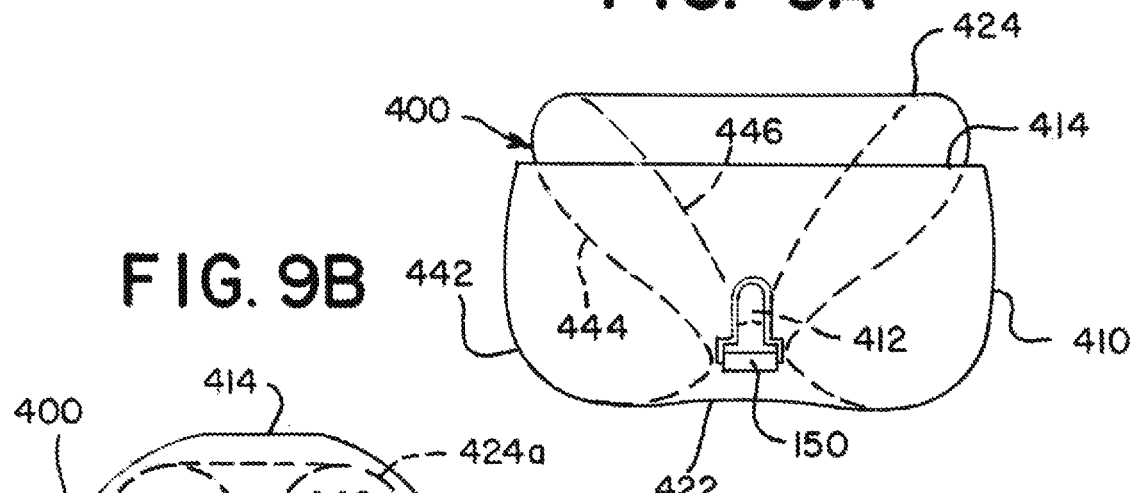
FIG. 9A is an illustration of an example implant having a tubular braid in another alternative predetermined shape according to aspects of the present invention.
Figure 9B:
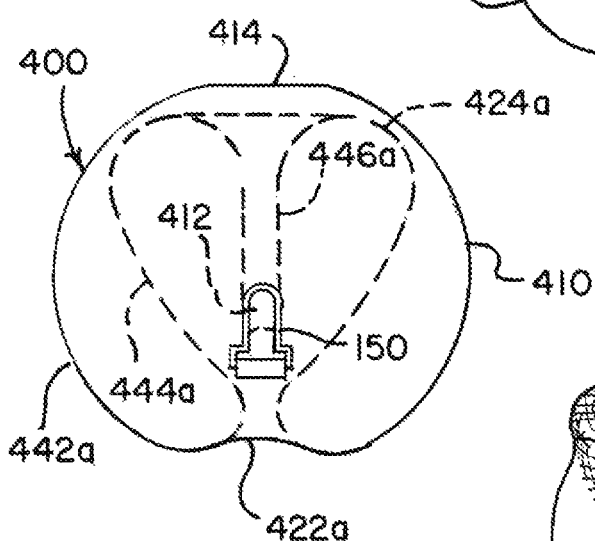
FIG. 9B is an illustration of the example implant illustrated in FIG. 9A with the tubular braid in an implanted shape according to aspects of the present invention.

FIG. 9A is an illustration of an example implant 400 having a tubular braid 410 in another alternative predetermined shape. FIG. 9B is an illustration of the example implant 400 illustrating the tubular braid 410 in an implanted shape. The tubular braid 410 can have an open end 414 and a pinched end 412. A detachment feature 150 can be attached to the braid 410 at the pinched end 412. The implant 400 can be formed in the predetermined shape, collapsed for delivery through a microcatheter, attached to a delivery system at the detachment feature 150, and implanted in the implanted shape.

As illustrated in FIG. 9A, when in the predetermined shape, the tubular braid 410 can include two inversions 422, 424, dividing the braid 410 into three segments 442, 444, 446. In the predetermined shape, the braid 410 can have an outer segment 442 extending from the open end 414 of the braid 410 to one of the inversions 422, an inner segment 446 extending from the pinched end 412 of the braid 410 to the other of the inversions 424, and a middle segment 444 extending between the two inversions 422, 424. When in the predetermined shape, the tubular braid 410 can be substantially radially symmetrical about a central vertical axis y (see FIG. 6A). FIG. 9A illustrates a profile of each segment 442, 444, 446.

Comparing the predetermined shape of the braid 410 illustrated in FIG. 9A to that of the braid 110 illustrated in FIG. 1A, the outer segments 142, 442 can be similar to each other, the middle segment 444 of the braid 410 illustrated in FIG. 9A can have a less pronounced "S" shape compared to the "S" shaped middle segment 144 illustrated in FIG. 1A, and the inner segment 446 can be conical or "V" shaped in profile with the pinch end 412 positioned near the inversion 422 adjacent the outer layer 442 rather than near the inversion 142 adjacent the inner layer 146 as illustrated in FIG. 1A. When implanted, the inner segment 446 can reshape to form a compaction resistant column.

The tubular braid 410 illustrated in FIG. 9A can be formed into the predetermined shape similar to as described in relation to FIG. 1A with some differences. The middle segment 444 illustrated in FIG. 9A can be formed to have a less pronounced "S" shape pattern compared to the "S" shaped pattern 144 illustrated in FIG. 1A. The middle segment 444 need not have bends positioned facilitate the movement of the braid 410 into a second implanted shape. The inner segment 446 can have a longer length as illustrated in FIG. 9A compared to the inner segment 146 illustrated in FIG. 1A. The inversion 424 adjacent the inner segment 446 can have a more acute curvature as illustrated in FIG. 9A compared to the corresponding inversion 124 illustrated in FIG. 1A.

As illustrated in FIG. 9B, when in the implanted shape, the braid 410 can have an outer layer 442a shaped to contact an aneurysm wall, a tulip or heart shaped sack 444a nested within the outer layer 442a, a proximal inversion 422a positioned to be placed at an aneurysm neck, a distal inversion 424a positioned to be placed near a distal portion of the aneurysm wall, and a compaction resistant column 446a extending within the sack 444a. The detachment feature 150 and pinched end 412 of the braid 410 can be positioned within the sack 444a near the proximal inversion 422a. The detachment feature 150 and pinched end 412 can be positioned to reduce the likelihood that the implant 400 becomes impacted.

Figure 10:
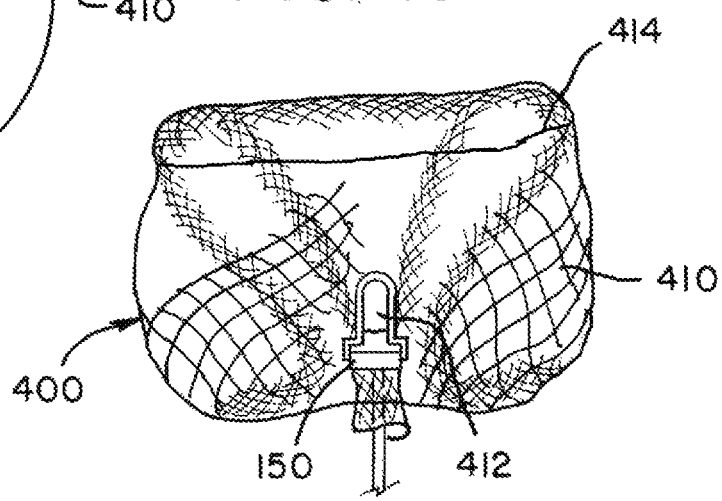
FIG. 10 is an illustration of an implant having a tubular braid in a predetermined shape similar to as illustrated in FIG. 9A according to aspects of the present invention.

FIG. 10 is an illustration of an example implant 400 having a tubular braid 410 in a predetermined shape similar to as illustrated in FIG. 9A.

Figure 11A:
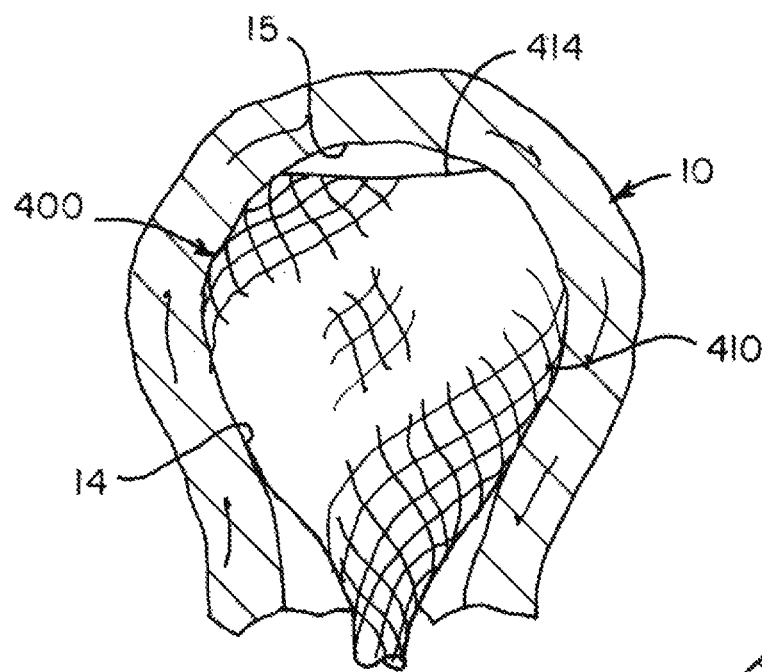
FIGS. 11A through 11E are illustrations of the implant illustrated in FIG. 10 showing the tubular braid expanding to the implanted shape similar to as illustrated in FIG. 9B according to aspects of the present invention.
Figure 11B:
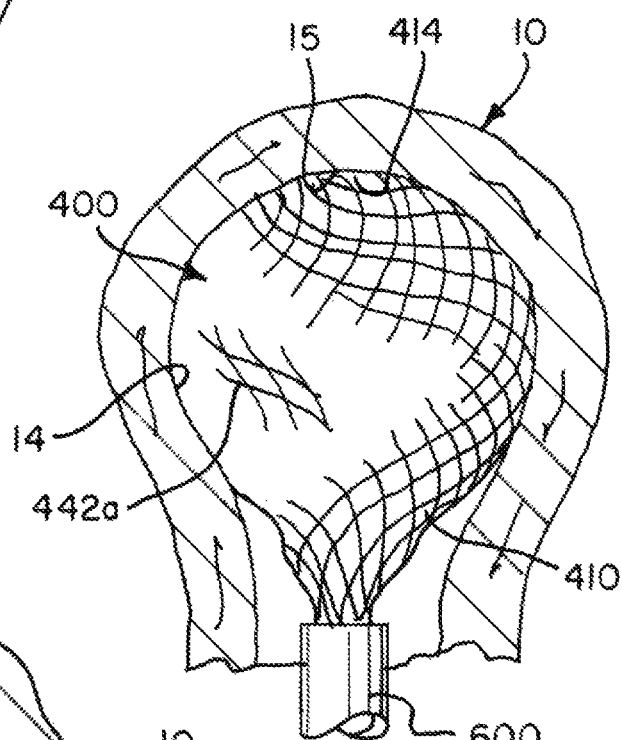
Figure 11C:
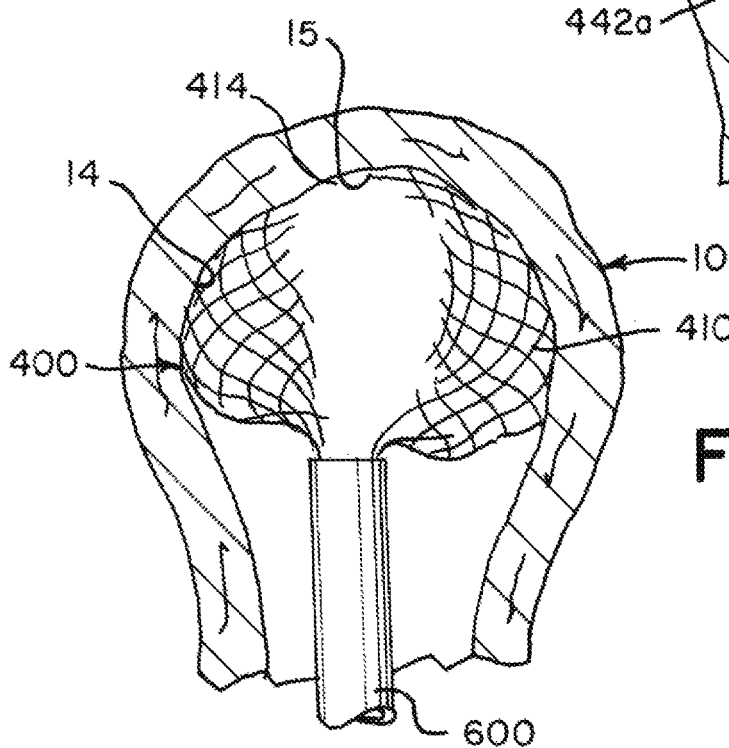
Figure 11D:
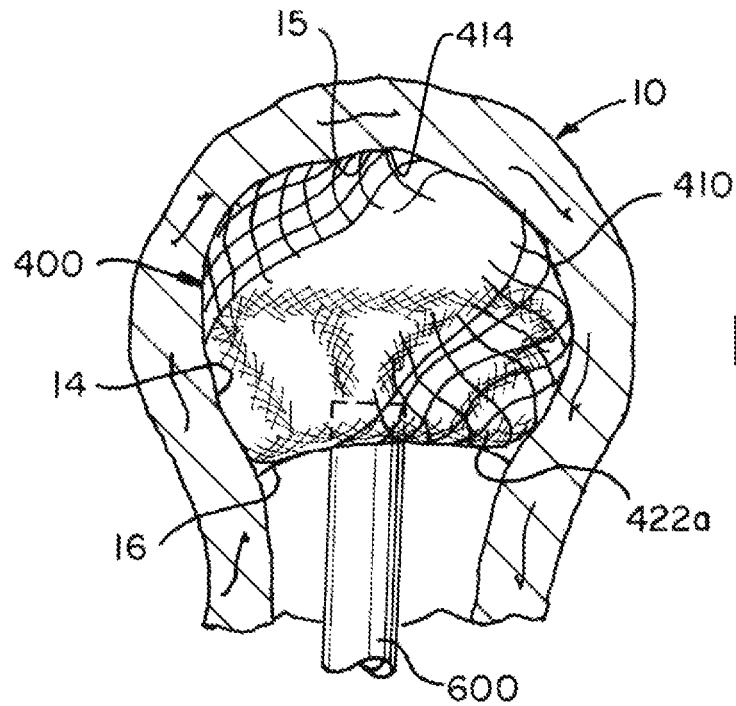
Figure 11E:
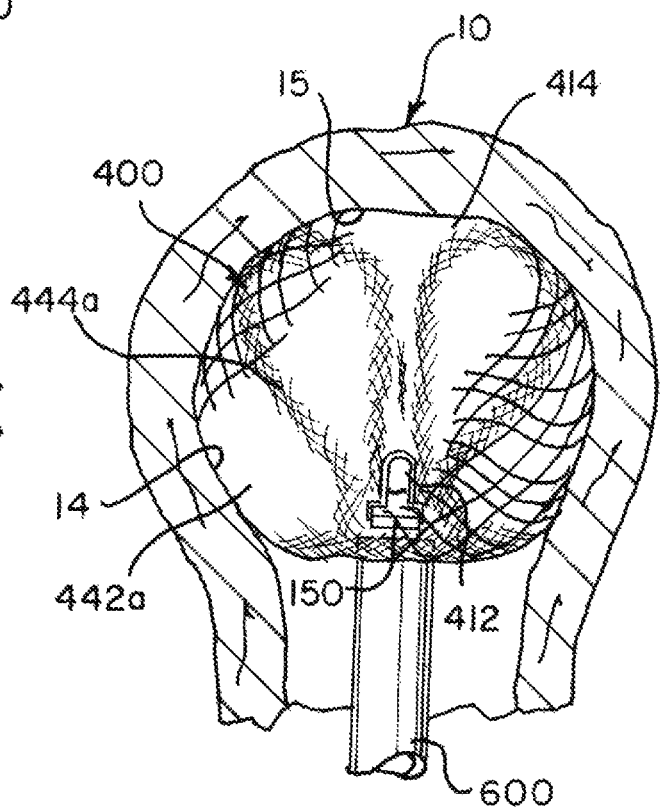

FIGS. 11A through 11E are illustrations of the example implant 400 illustrated in FIG. 10 showing the tubular braid 410 expanding to the implanted shape within a mock aneurysm 10 similar to as illustrated in FIG. 9B. As illustrated in FIG. 11A, the open end 414 can exit the microcatheter first and expand within the aneurysm 10. As illustrated in FIG. 11B, a distal portion of the braid 410 corresponding to the outer layer 442 in the predetermined shape can expand to appose the aneurysm wall 14 forming the outer later 442a in the implanted shape. As illustrated in FIG. 11C, the braid 410 can begin to invert as the braid 410 is further pushed distally from the microcatheter 600. As illustrated in FIG. 11D, the proximal inversion 422a can be placed at the aneurysm neck 16 as the tulip shaped sack 444a expands within the outer layer 442a. As illustrated in FIG. 11E, the braid 410 can be shaped in the implanted shape within the aneurysm 10 similar to as illustrated in FIG. 9B.

The tubular braid 110, 210, 310, 410 of the example implants 100, 200, 300, 400 can include memory shape material that can be heat set to a predetermined shape, can be deformed for delivery through a catheter, and can self-expand to an implanted shape that is based on the predetermined shape and confined by the anatomy of the aneurysm in which it is implanted.

The example implants 100, 200, 300, 400 described herein can rely on a radial outward force to anchor the implant within the sac of an aneurysm. To this end, the braid 110, 210, 310, 410 can be shaped to a predetermined shape having a diameter that is greater than its height so that the braid is radially constricted when implanted in an aneurysm. The ratio of diameter to height of the braid 110, 210, 310, 410 in a respective predetermined shape can be within the range of 2:1 to 1:3 to treat aneurysms of many known sizes and shapes.

The descriptions contained herein are examples of embodiments of the invention and are not intended in any way to limit the scope of the invention. As described herein, the invention contemplates many variations and modifications of the implant, including alternative materials, alternative geometries, alternative detachment features, alternative delivery systems, alternative means for forming a braid into a predetermined shape, alternative treatment methods, etc. These modifications would be apparent to those having ordinary skill in the art to which this invention relates and are intended to be within the scope of the claims which follow.

What is claimed is:

1. A method comprising:
 selecting a tubular braid comprising an open end and a pinched end; and
 shaping the tubular braid to a predetermined shape as follows:
  inverting the tubular braid to form a distal inversion;
  shaping an inner segment of the tubular braid extending from the distal inversion to the pinched end;
  inverting the tubular braid to form a proximal inversion by moving the open end over at least a portion of the braid;
  shaping a middle segment of the tubular braid extending between the proximal inversion and the distal inversion;
  positioning the middle segment to surround the inner segment;
  shaping an outer segment of the tubular braid extending between the open end and the proximal inversion;
  positioning the open end to encircle the middle segment between the proximal inversion and the distal inversion such that the middle segment is only partially surrounded by the outer segment; and
  positioning the pinched end distal of the proximal inversion.

2. The method of claim 1, wherein shaping the tubular braid to the predetermined shape further comprises shaping the open end to comprise a diameter greater than or approximately equal to a maximum diameter of the middle segment.

3. The method of claim 1,
 wherein shaping the tubular braid to the predetermined shape further comprises forming the tubular braid to be implantable in a first aneurysm comprising a first height and in a second aneurysm comprising a second height less than the first height, such that the tubular braid comprises a first implanted shape when implanted in the first aneurysm and a second implanted shape when implanted in the second aneurysm, the first implanted shape based on the predetermined shape when constrained by the first aneurysm and the second implanted shape based on the predetermined shape when constrained by the second aneurysm.

4. The method of claim 3, further comprising:
 reshaping the tubular braid to one of the first implanted shape or the second implanted shape,
 wherein reshaping the tubular braid to the first implanted shape comprises:
  reshaping the outer segment to form an outer braid layer that apposes an aneurysm wall of the first aneurysm;
  positioning the proximal inversion approximate an aneurysm neck of the first aneurysm; and
  reshaping the middle segment to form a sack of the tubular braid that apposes the outer braid layer and the aneurysm wall of the first aneurysm, and
 wherein reshaping the tubular braid to the second implanted shape comprises:
  reshaping the outer segment to form an outer braid layer that apposes an aneurysm wall of the second aneurysm;
  positioning the proximal inversion approximate an aneurysm neck of the second aneurysm; and
  folding the middle segment to form a middle braid layer apposing the outer layer and an inner braid layer apposing the middle braid layer.

5. The method of claim 4,
 wherein shaping the tubular braid to the predetermined shape further comprises:
  forming a bend in the middle segment, and
 wherein reshaping the tubular braid to the second implanted shape further comprises folding the bend to form a boundary between the middle braid layer and the inner braid layer.

6. The method of claim 4,
 wherein reshaping the tubular braid to the first implanted shape further comprises suspending the pinched end within the sack, and
 wherein reshaping the tubular braid to the second implanted shape further comprises positioning the proximal inversion to encircle the pinched end.

7. The method of claim 4,
 wherein reshaping the tubular braid to the first implanted shape further comprises encircling the sack with the open end, and
 wherein reshaping the tubular braid to the second implanted shape further comprises positioning the open end to encircle a fold separating the middle braid layer and the inner braid layer.

8. The method of claim 1, wherein shaping the tubular braid to the predetermined shape further comprises forming the tubular braid to be implantable in a first aneurysm comprising a first diameter measuring about 4 mm and a first height measuring about 6 mm, a second aneurysm comprising a second diameter measuring about 5 mm and a second height measuring about 8 mm, and a third aneurysm comprising a third diameter measuring about 6 mm and a third height measuring about 6 mm.

9. The method of claim 1, wherein shaping the tubular braid to the predetermined shape further comprises forming the tubular braid to be suitable for treating a continuum of aneurysm sizes, the continuum bounded by and including diameters between about 4 mm and about 5 mm and heights between about 6 mm and about 8 mm.

10. The method of claim 1, further comprising:
 positioning the proximal inversion in a proximal direction in relation to a plane defining a boundary between an aneurysm and blood vessel branches.

11. The method of claim 1, further comprising:
 wherein the tubular braid comprising an implant;
 collapsing the implant to fit within a microcatheter;
 pushing the implant at the pinched end of the tubular braid through a majority of the length of the microcatheter to an aneurysm within a patient,
 wherein the tubular braid is unsheathed within the microcatheter as it is pushed through the majority of the length; and implanting the implant in the aneurysm,
 wherein the tubular braid is implanted unsheathed within the aneurysm, and
 wherein the tubular braid is moved to an implanted shape based on the predetermined shape when implanted.

12. A method for aneurysm treatment, the method comprising:
 delivering a tubular braid comprising an open end and a pinched end through vasculature to an aneurysm;

apposing the open end and a first segment of the tubular braid extending from the open end to a wall of the aneurysm;

inverting the tubular braid at a neck of the aneurysm to form a proximal inversion and an inverted second segment of the tubular braid extending into the aneurysm from the proximal inversion; and positioning the second segment of the tubular braid such that the second segment is only partially surrounded by the first segment; and positioning the pinched end distal of the proximal inversion.

13. The method of claim 12, further comprising:

shaping the second segment to form a sack apposing a portion of the wall and the first segment;

suspending the pinched end within the sack; and stabilizing the tubular braid in a first implanted shape wherein the open end and the first segment appose the aneurysm wall, the proximal inversion is positioned at the aneurysm neck, the second segment of the tubular braid is only partially surrounded by the first segment, the second segment forms the sack apposing the portion of the wall and the first segment, and the pinched end is suspended within the sack.

14. The method of claim 13, further comprising:

delivering a substantially identical tubular braid that is substantially identical to the tubular braid stabilized in the first implanted shape to a smaller aneurysm having a smaller internal dimension compared to the aneurysm;

apposing an open end of the substantially identical tubular braid and a first segment of the substantially identical tubular braid extending from the open end of the substantially identical tubular braid to a wall of the smaller aneurysm;

inverting the substantially identical tubular braid at a neck of the smaller aneurysm to form a proximal inversion and an inverted second segment of the substantially identical tubular braid extending into the smaller aneurysm from the proximal inversion of the substantially identical tubular braid;

inverting the substantially identical tubular braid approximate the open end of the substantially identical tubular braid to form a distal inversion and a third segment of the substantially identical tubular braid extending from the distal inversion to the neck of the smaller aneurysm;

positioning the pinched end of the substantially identical tubular braid such that the pinched end of the substantially identical tubular braid is encircled by the proximal inversion of the substantially identical tubular braid; and stabilizing the substantially identical tubular braid in a second implanted shape wherein the open end and the first segment of the substantially identical tubular braid appose the wall of the smaller aneurysm, the proximal inversion of the substantially identical tubular braid is positioned at the aneurysm neck of the smaller aneurysm, the second segment of the substantially identical tubular braid extends from the proximal inversion to the distal inversion of the substantially identical tubular braid, the third segment of the substantially identical tubular braid extends from the distal inversion to the pinched end of the substantially identical tubular braid, and the pinched end of the substantially identical tubular braid is encircled by the proximal inversion of the substantially identical tubular braid.

15. The method of claim 14, further comprising:

implanting the tubular braid in the first implanted shape in the aneurysm comprising a first diameter measuring about 5 mm and a first height measuring about 8 mm; and implanting the substantially identical tubular braid in the second implanted shape in the smaller aneurysm comprising a second diameter measuring about 4 mm and a second height measuring about 6 mm.

16. The method of claim 14, further comprising:

implanting the tubular braid in the first implanted shape in the aneurysm comprising a first diameter measuring about 6 mm and a first height measuring about 6 mm; and implanting the substantially identical tubular braid in the second implanted shape in the smaller aneurysm comprising a second diameter measuring about 4 mm and a second height measuring about 6 mm.

17. The method of claim 14, further comprising:

inverting the tubular braid approximate a distal portion of the aneurysm wall to form a distal inversion and a third segment extending from the distal inversion to the neck; and positioning the third segment to form a compaction resistant post configured to resist compaction of the aneurysm.

18. The method of claim 14, further comprising:

shaping the substantially identical tubular braid to comprise a plurality of undulations extending to and from a central axis extending from a distal portion of the aneurysm wall and centrally through the aneurysm neck.

* * * * *